(12) United States Patent
Ludwig et al.

(10) Patent No.: US 10,050,700 B2
(45) Date of Patent: Aug. 14, 2018

(54) COMMUNICATIONS IN A MEDICAL DEVICE SYSTEM WITH TEMPORAL OPTIMIZATION

(71) Applicant: CARDIAC PACEMAKERS, INC., St. Paul, MN (US)

(72) Inventors: Jacob M. Ludwig, Isanti, MN (US); Michael J. Kane, Roseville, MN (US); Brendan E. Koop, Ham Lake, MN (US); William J. Linder, Golden Valley, MN (US); Keith R. Maile, New Brighton, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 254 days.

(21) Appl. No.: 15/058,412

(22) Filed: Mar. 2, 2016

(65) Prior Publication Data

US 2016/0277097 A1 Sep. 22, 2016

Related U.S. Application Data

(60) Provisional application No. 62/134,752, filed on Mar. 18, 2015.

(51) Int. Cl.
*H04B 7/24* (2006.01)
*H04L 1/12* (2006.01)
(Continued)

(52) U.S. Cl.
CPC ............ *H04B 7/24* (2013.01); *A61B 5/0028* (2013.01); *A61N 1/362* (2013.01);
(Continued)

(58) Field of Classification Search
USPC .................. 455/41.1; 607/30–32, 59–60
See application file for complete search history.

(56) References Cited

U.S. PATENT DOCUMENTS

| 3,835,864 A | 9/1974 | Rasor et al. |
| 3,943,936 A | 3/1976 | Rasor et al. |
| (Continued) | | |

FOREIGN PATENT DOCUMENTS

| AU | 2008279789 B2 | 10/2011 |
| AU | 2008329620 B2 | 5/2014 |
| (Continued) | | |

OTHER PUBLICATIONS

US 8,886,318, 11/2014, Jacobson et al. (withdrawn)
(Continued)

*Primary Examiner* — Nay A Maung
*Assistant Examiner* — Erica Fleming-Hall
(74) *Attorney, Agent, or Firm* — Seager, Tufte & Wickhem LLP

(57) ABSTRACT

Systems and methods for managing communication strategies between implanted medical devices. Methods include temporal optimization relative to one or more identified conditions in the body. A selected characteristic, such as a signal representative or linked to a biological function, is assessed to determine its likely impact on communication capabilities, and one or more communication strategies may be developed to optimize intra-body communication.

19 Claims, 10 Drawing Sheets

(51) Int. Cl.
 *A61N 1/362* (2006.01)
 *A61N 1/372* (2006.01)
 *A61B 5/00* (2006.01)
 *H04B 13/00* (2006.01)

(52) U.S. Cl.
 CPC ..... *A61N 1/37217* (2013.01); *A61N 1/37288* (2013.01); *H04B 13/005* (2013.01); *H04L 1/12* (2013.01); *A61B 2560/0209* (2013.01); *A61N 1/37252* (2013.01)

(56) References Cited

U.S. PATENT DOCUMENTS

| | | | |
|---|---|---|---|
| 4,142,530 A | 3/1979 | Wittkampf | |
| 4,151,513 A | 4/1979 | Menken et al. | |
| 4,157,720 A | 6/1979 | Greatbatch | |
| RE30,366 E | 8/1980 | Rasor et al. | |
| 4,250,884 A | 2/1981 | Hartlaub et al. | |
| 4,256,115 A | 3/1981 | Bilitch | |
| 4,263,919 A | 4/1981 | Levin | |
| 4,310,000 A | 1/1982 | Lindemans | |
| 4,312,354 A | 1/1982 | Walters | |
| 4,323,081 A | 4/1982 | Wiebusch | |
| 4,357,946 A | 11/1982 | Dutcher et al. | |
| 4,365,639 A | 12/1982 | Goldreyer | |
| 4,440,173 A | 4/1984 | Hudziak et al. | |
| 4,476,868 A | 10/1984 | Thompson | |
| 4,522,208 A | 6/1985 | Buffet | |
| 4,556,063 A | 12/1985 | Thompson et al. | |
| 4,562,841 A | 1/1986 | Brockway et al. | |
| 4,593,702 A | 6/1986 | Kepski et al. | |
| 4,593,955 A | 6/1986 | Leiber | |
| 4,630,611 A | 12/1986 | King | |
| 4,635,639 A | 1/1987 | Hakala et al. | |
| 4,674,508 A | 6/1987 | DeCote | |
| 4,712,554 A | 12/1987 | Garson | |
| 4,729,376 A | 3/1988 | DeCote | |
| 4,754,753 A | 7/1988 | King | |
| 4,759,366 A | 7/1988 | Callaghan | |
| 4,787,389 A | 11/1988 | Tarjan | |
| 4,793,353 A | 12/1988 | Borkan | |
| 4,819,662 A | 4/1989 | Heil et al. | |
| 4,858,610 A | 8/1989 | Callaghan et al. | |
| 4,886,064 A | 12/1989 | Strandberg | |
| 4,928,688 A | 5/1990 | Mower | |
| 4,967,746 A | 11/1990 | Vandegriff | |
| 4,987,897 A | 1/1991 | Funke | |
| 4,989,602 A | 2/1991 | Sholder et al. | |
| 5,012,806 A | 5/1991 | De Bellis | |
| 5,036,849 A | 8/1991 | Hauck et al. | |
| 5,058,581 A | 10/1991 | Silvian | |
| 5,078,134 A | 1/1992 | Heilman et al. | |
| 5,109,845 A | 5/1992 | Yuuchi et al. | |
| 5,113,859 A | 5/1992 | Funke | |
| 5,117,824 A | 6/1992 | Keimel et al. | |
| 5,127,401 A | 7/1992 | Grevious et al. | |
| 5,133,353 A | 7/1992 | Hauser | |
| 5,144,950 A | 9/1992 | Stoop et al. | |
| 5,170,784 A | 12/1992 | Ramon et al. | |
| 5,179,945 A | 1/1993 | Van Hofwegen et al. | |
| 5,193,539 A | 3/1993 | Schulman et al. | |
| 5,193,540 A | 3/1993 | Schulman et al. | |
| 5,241,961 A | 9/1993 | Henry | |
| 5,243,977 A | 9/1993 | Trabucco et al. | |
| 5,269,326 A | 12/1993 | Verrier | |
| 5,284,136 A | 2/1994 | Hauck et al. | |
| 5,300,107 A | 4/1994 | Stokes et al. | |
| 5,301,677 A | 4/1994 | Hsung | |
| 5,312,439 A | 5/1994 | Loeb | |
| 5,313,953 A | 5/1994 | Yomtov et al. | |
| 5,314,459 A | 5/1994 | Swanson et al. | |
| 5,318,597 A | 6/1994 | Hauck et al. | |
| 5,324,316 A | 6/1994 | Schulman et al. | |
| 5,331,966 A | 7/1994 | Bennett et al. | |
| 5,334,222 A | 8/1994 | Salo et al. | |
| 5,342,408 A | 8/1994 | Decoriolis et al. | |
| 5,372,606 A | 12/1994 | Lang et al. | |
| 5,376,106 A | 12/1994 | Stahmann et al. | |
| 5,383,915 A | 1/1995 | Adams | |
| 5,388,578 A | 2/1995 | Yomtov et al. | |
| 5,404,877 A * | 4/1995 | Nolan ............. | A61B 5/0006 600/484 |
| 5,405,367 A | 4/1995 | Schulman et al. | |
| 5,411,031 A | 5/1995 | Yomtov | |
| 5,411,525 A | 5/1995 | Swanson et al. | |
| 5,411,535 A | 5/1995 | Fujii et al. | |
| 5,456,691 A | 10/1995 | Snell | |
| 5,466,246 A | 11/1995 | Silvian | |
| 5,468,254 A | 11/1995 | Hahn et al. | |
| 5,522,866 A | 6/1996 | Fernald | |
| 5,540,727 A | 7/1996 | Tockman et al. | |
| 5,545,186 A * | 8/1996 | Olson ............. | A61B 5/042 607/14 |
| 5,545,202 A | 8/1996 | Dahl et al. | |
| 5,591,214 A | 1/1997 | Lu | |
| 5,620,466 A | 4/1997 | Haefner et al. | |
| 5,634,938 A | 6/1997 | Swanson et al. | |
| 5,662,688 A | 9/1997 | Haefner et al. | |
| 5,674,259 A | 10/1997 | Gray | |
| 5,683,426 A | 11/1997 | Greenhut et al. | |
| 5,683,432 A | 11/1997 | Goedeke et al. | |
| 5,720,770 A | 2/1998 | Nappholz et al. | |
| 5,728,154 A | 3/1998 | Crossett et al. | |
| 5,741,314 A | 4/1998 | Daly et al. | |
| 5,741,315 A | 4/1998 | Lee et al. | |
| 5,752,976 A | 5/1998 | Duffin et al. | |
| 5,752,977 A | 5/1998 | Grevious et al. | |
| 5,755,736 A | 5/1998 | Gillberg et al. | |
| 5,759,199 A | 6/1998 | Snell et al. | |
| 5,774,501 A | 6/1998 | Halpern et al. | |
| 5,792,202 A | 8/1998 | Rueter | |
| 5,792,203 A | 8/1998 | Schroeppel | |
| 5,792,205 A | 8/1998 | Alt et al. | |
| 5,792,208 A | 8/1998 | Gray | |
| 5,814,089 A | 9/1998 | Stokes et al. | |
| 5,827,216 A | 10/1998 | Igo et al. | |
| 5,836,985 A | 11/1998 | Goyal et al. | |
| 5,836,987 A | 11/1998 | Baumann et al. | |
| 5,842,977 A | 12/1998 | Lesho et al. | |
| 5,855,593 A | 1/1999 | Olson et al. | |
| 5,873,894 A | 2/1999 | Vandegriff et al. | |
| 5,891,184 A | 4/1999 | Lee et al. | |
| 5,897,586 A | 4/1999 | Molina | |
| 5,899,876 A | 5/1999 | Flower | |
| 5,899,928 A | 5/1999 | Sholder et al. | |
| 5,919,214 A | 7/1999 | Ciciarelli et al. | |
| 5,935,078 A | 8/1999 | Feierbach | |
| 5,941,906 A | 8/1999 | Barreras et al. | |
| 5,954,757 A | 9/1999 | Gray | |
| 5,978,713 A | 11/1999 | Prutchi et al. | |
| 5,991,660 A | 11/1999 | Goyal | |
| 5,999,848 A | 12/1999 | Gord et al. | |
| 5,999,857 A | 12/1999 | Weijand et al. | |
| 6,026,320 A | 2/2000 | Carlson et al. | |
| 6,044,298 A | 3/2000 | Salo et al. | |
| 6,044,300 A | 3/2000 | Gray | |
| 6,055,454 A | 4/2000 | Heemels | |
| 6,073,050 A | 6/2000 | Griffith | |
| 6,076,016 A | 6/2000 | Feierbach | |
| 6,080,187 A | 6/2000 | Alt et al. | |
| 6,083,248 A | 7/2000 | Thompson | |
| 6,106,551 A | 8/2000 | Crossett et al. | |
| 6,115,636 A | 9/2000 | Ryan | |
| 6,141,581 A | 10/2000 | Olson et al. | |
| 6,141,588 A | 10/2000 | Cox et al. | |
| 6,141,592 A | 10/2000 | Pauly | |
| 6,144,879 A | 11/2000 | Gray | |
| 6,162,195 A | 12/2000 | Igo et al. | |
| 6,164,284 A | 12/2000 | Schulman et al. | |
| 6,167,310 A | 12/2000 | Grevious | |
| 6,208,894 B1 | 3/2001 | Schulman et al. | |
| 6,211,799 B1 | 4/2001 | Post et al. | |
| 6,221,011 B1 | 4/2001 | Bardy | |
| 6,240,316 B1 | 5/2001 | Richmond et al. | |

(56) References Cited

U.S. PATENT DOCUMENTS

| | | | |
|---|---|---|---|
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,298,271 B1 | 10/2001 | Weijand |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 * | 8/2002 | Khair | A61B 5/0006 128/903 |
| 6,442,426 B1 | 8/2002 | Kroll |
| 6,442,432 B2 | 8/2002 | Lee |
| 6,443,891 B1 * | 9/2002 | Grevious | A61B 5/0002 128/903 |
| 6,445,953 B1 * | 9/2002 | Bulkes | A61N 1/37211 607/126 |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 * | 9/2004 | Sloman | A61N 1/3712 607/28 |
| 6,788,974 B2 | 9/2004 | Bardy et al. |
| 6,804,558 B2 | 10/2004 | Haller et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 * | 8/2005 | Schloss | A61N 1/3622 607/9 |
| 6,957,107 B2 | 10/2005 | Rogers et al. |
| 6,978,176 B2 | 12/2005 | Lattouf |
| 6,985,773 B2 | 1/2006 | Von Arx et al. |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,110,824 B2 | 9/2006 | Amundson et al. |
| 7,120,504 B2 | 10/2006 | Osypka |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,790 B2 | 4/2007 | Thompson et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B1 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |

(56) References Cited

U.S. PATENT DOCUMENTS

| | | | |
|---|---|---|---|
| 7,410,497 | B2 | 8/2008 | Hastings et al. |
| 7,425,200 | B2 | 9/2008 | Brockway et al. |
| 7,433,739 | B1 | 10/2008 | Salys et al. |
| 7,496,409 | B2 | 2/2009 | Greenhut et al. |
| 7,496,410 | B2 | 2/2009 | Heil |
| 7,502,652 | B2 | 3/2009 | Gaunt et al. |
| 7,512,448 | B2 | 3/2009 | Malick et al. |
| 7,515,969 | B2 | 4/2009 | Tockman et al. |
| 7,526,342 | B2 | 4/2009 | Chin et al. |
| 7,529,589 | B2 | 5/2009 | Williams et al. |
| 7,532,933 | B2 | 5/2009 | Hastings et al. |
| 7,536,222 | B2 | 5/2009 | Bardy et al. |
| 7,539,541 | B2 | 5/2009 | Quiles et al. |
| 7,544,197 | B2 | 6/2009 | Kelsch et al. |
| 7,558,631 | B2 | 7/2009 | Cowan et al. |
| 7,565,195 | B1 | 7/2009 | Kroll et al. |
| 7,584,002 | B2 | 9/2009 | Burnes et al. |
| 7,590,455 | B2 | 9/2009 | Heruth et al. |
| 7,606,621 | B2 | 10/2009 | Brisken et al. |
| 7,610,088 | B2 | 10/2009 | Chinchoy |
| 7,610,092 | B2 | 10/2009 | Cowan et al. |
| 7,610,099 | B2 | 10/2009 | Almendinger et al. |
| 7,610,104 | B2 | 10/2009 | Kaplan et al. |
| 7,616,991 | B2 | 11/2009 | Mann et al. |
| 7,617,001 | B2 | 11/2009 | Penner et al. |
| 7,617,007 | B2 | 11/2009 | Williams et al. |
| 7,630,767 | B1 | 12/2009 | Poore et al. |
| 7,634,313 | B1 | 12/2009 | Kroll et al. |
| 7,637,867 | B2 | 12/2009 | Zdeblick |
| 7,640,060 | B2 | 12/2009 | Zdeblick |
| 7,647,109 | B2 | 1/2010 | Hastings et al. |
| 7,650,186 | B2 | 1/2010 | Hastings et al. |
| 7,657,311 | B2 | 2/2010 | Bardy et al. |
| 7,668,596 | B2 | 2/2010 | Von Arx et al. |
| 7,691,047 | B2 | 4/2010 | Ferrari |
| 7,702,392 | B2 | 4/2010 | Echt et al. |
| 7,713,194 | B2 | 5/2010 | Zdeblick |
| 7,713,195 | B2 | 5/2010 | Zdeblick |
| 7,729,783 | B2 | 6/2010 | Michels et al. |
| 7,734,333 | B2 | 6/2010 | Ghanem et al. |
| 7,734,343 | B2 | 6/2010 | Ransbury et al. |
| 7,738,958 | B2 | 6/2010 | Zdeblick et al. |
| 7,738,964 | B2 | 6/2010 | Von Arx et al. |
| 7,742,812 | B2 | 6/2010 | Ghanem et al. |
| 7,742,816 | B2 | 6/2010 | Masoud et al. |
| 7,742,822 | B2 | 6/2010 | Masoud et al. |
| 7,743,151 | B2 | 6/2010 | Vallapureddy et al. |
| 7,747,335 | B2 | 6/2010 | Williams |
| 7,751,881 | B2 | 7/2010 | Cowan et al. |
| 7,758,521 | B2 | 7/2010 | Morris et al. |
| 7,761,150 | B2 | 7/2010 | Ghanem et al. |
| 7,761,164 | B2 | 7/2010 | Verhoef et al. |
| 7,765,001 | B2 | 7/2010 | Echt et al. |
| 7,769,452 | B2 | 8/2010 | Ghanem et al. |
| 7,792,588 | B2 | 9/2010 | Harding |
| 7,797,059 | B1 | 9/2010 | Bornzin et al. |
| 7,801,596 | B2 | 9/2010 | Fischell et al. |
| 7,809,438 | B2 | 10/2010 | Echt et al. |
| 7,840,281 | B2 | 11/2010 | Kveen et al. |
| 7,844,348 | B2 | 11/2010 | Swoyer et al. |
| 7,846,088 | B2 | 12/2010 | Ness |
| 7,848,815 | B2 | 12/2010 | Brisken et al. |
| 7,848,823 | B2 | 12/2010 | Drasler et al. |
| 7,860,455 | B2 | 12/2010 | Fukumoto et al. |
| 7,871,433 | B2 | 1/2011 | Lattouf |
| 7,877,136 | B1 | 1/2011 | Moffitt et al. |
| 7,877,142 | B2 | 1/2011 | Moaddeb et al. |
| 7,881,798 | B2 | 2/2011 | Miesel et al. |
| 7,881,810 | B1 | 2/2011 | Chitre et al. |
| 7,890,173 | B2 | 2/2011 | Brisken et al. |
| 7,890,181 | B2 | 2/2011 | Denzene et al. |
| 7,890,192 | B1 | 2/2011 | Kelsch et al. |
| 7,894,894 | B2 | 2/2011 | Stadler et al. |
| 7,894,907 | B2 | 2/2011 | Cowan et al. |
| 7,894,910 | B2 | 2/2011 | Cowan et al. |
| 7,894,915 | B1 | 2/2011 | Chitre et al. |
| 7,899,537 | B1 | 3/2011 | Kroll et al. |
| 7,899,541 | B2 | 3/2011 | Cowan et al. |
| 7,899,542 | B2 | 3/2011 | Cowan et al. |
| 7,899,554 | B2 | 3/2011 | Williams et al. |
| 7,901,360 | B1 | 3/2011 | Yang et al. |
| 7,904,170 | B2 | 3/2011 | Harding |
| 7,907,993 | B2 | 3/2011 | Ghanem et al. |
| 7,920,928 | B1 | 4/2011 | Yang et al. |
| 7,925,343 | B1 | 4/2011 | Min et al. |
| 7,930,040 | B1 | 4/2011 | Kelsch et al. |
| 7,937,135 | B2 | 5/2011 | Ghanem et al. |
| 7,937,148 | B2 | 5/2011 | Jacobson |
| 7,937,161 | B2 | 5/2011 | Hastings et al. |
| 7,941,214 | B2 | 5/2011 | Kleckner et al. |
| 7,945,333 | B2 | 5/2011 | Jacobson |
| 7,946,997 | B2 | 5/2011 | Hübinette |
| 7,949,404 | B2 | 5/2011 | Hill |
| 7,949,405 | B2 | 5/2011 | Feher |
| 7,953,493 | B2 | 5/2011 | Fowler et al. |
| 7,962,202 | B2 | 6/2011 | Bhunia |
| 7,974,702 | B1 | 7/2011 | Fain et al. |
| 7,979,136 | B2 | 7/2011 | Young et al. |
| 7,983,753 | B2 | 7/2011 | Severin |
| 3,010,209 | A1 | 8/2011 | Jacobson |
| 7,991,467 | B2 | 8/2011 | Markowitz et al. |
| 7,991,471 | B2 | 8/2011 | Ghanem et al. |
| 7,996,087 | B2 | 8/2011 | Cowan et al. |
| 8,000,791 | B2 | 8/2011 | Sunagawa et al. |
| 8,000,807 | B2 | 8/2011 | Morris et al. |
| 8,001,975 | B2 | 8/2011 | DiSilvestro et al. |
| 8,002,700 | B2 | 8/2011 | Ferek-Petric et al. |
| 8,019,419 | B1 | 9/2011 | Panescu et al. |
| 8,019,434 | B2 | 9/2011 | Quiles et al. |
| 8,027,727 | B2 * | 9/2011 | Freeberg ............ A61N 1/37211 128/903 |
| 8,027,729 | B2 | 9/2011 | Sunagawa et al. |
| 8,032,219 | B2 | 10/2011 | Neumann et al. |
| 8,036,743 | B2 | 10/2011 | Savage et al. |
| 8,046,079 | B2 | 10/2011 | Bange et al. |
| 8,046,080 | B2 * | 10/2011 | Von Arx ................. A61N 1/08 607/60 |
| 8,050,297 | B2 | 11/2011 | Delmain et al. |
| 8,050,759 | B2 | 11/2011 | Stegemann et al. |
| 8,050,774 | B2 | 11/2011 | Kveen et al. |
| 8,055,345 | B2 | 11/2011 | Li et al. |
| 8,055,350 | B2 | 11/2011 | Roberts |
| 8,060,212 | B1 | 11/2011 | Rios et al. |
| 8,065,018 | B2 | 11/2011 | Haubrich et al. |
| 8,073,542 | B2 | 12/2011 | Doerr |
| 8,078,278 | B2 | 12/2011 | Penner |
| 8,078,283 | B2 | 12/2011 | Cowan et al. |
| 8,095,123 | B2 | 1/2012 | Gray |
| 8,102,789 | B2 | 1/2012 | Rosar et al. |
| 8,103,359 | B2 | 1/2012 | Reddy |
| 8,103,361 | B2 | 1/2012 | Moser |
| 8,112,148 | B2 | 2/2012 | Giftakis et al. |
| 8,114,021 | B2 | 2/2012 | Robertson et al. |
| 8,121,680 | B2 | 2/2012 | Falkenberg et al. |
| 8,123,684 | B2 | 2/2012 | Zdeblick |
| 8,126,545 | B2 | 2/2012 | Flach et al. |
| 8,131,334 | B2 | 3/2012 | Lu et al. |
| 8,140,161 | B2 | 3/2012 | Willerton et al. |
| 8,150,521 | B2 | 4/2012 | Crowley et al. |
| 8,160,672 | B2 | 4/2012 | Kim et al. |
| 8,160,702 | B2 | 4/2012 | Mann et al. |
| 8,160,704 | B2 | 4/2012 | Freeberg |
| 8,165,694 | B2 | 4/2012 | Carbanaru et al. |
| 8,175,715 | B1 | 5/2012 | Cox |
| 8,180,451 | B2 | 5/2012 | Hickman et al. |
| 8,185,213 | B2 | 5/2012 | Kveen et al. |
| 8,187,161 | B2 | 5/2012 | Li et al. |
| 8,204,595 | B2 | 6/2012 | Pianca et al. |
| 8,204,605 | B2 | 6/2012 | Hastings et al. |
| 8,209,014 | B2 | 6/2012 | Doerr |
| 8,214,043 | B2 | 7/2012 | Matos |
| 8,224,244 | B2 | 7/2012 | Kim et al. |
| 8,233,985 | B2 | 7/2012 | Bulkes et al. |
| 8,265,748 | B2 | 9/2012 | Liu et al. |

(56) References Cited

U.S. PATENT DOCUMENTS

| | | | |
|---|---|---|---|
| 8,265,757 B2 | 9/2012 | Mass et al. | |
| 8,280,521 B2 | 10/2012 | Haubrich et al. | |
| 8,285,387 B2 | 10/2012 | Utsi et al. | |
| 8,290,589 B2* | 10/2012 | Bange | A61N 1/37223 607/16 |
| 8,290,598 B2 | 10/2012 | Boon et al. | |
| 8,290,600 B2 | 10/2012 | Hastings et al. | |
| 8,295,939 B2 | 10/2012 | Jacobson | |
| 8,301,254 B2 | 10/2012 | Mosesov et al. | |
| 8,315,701 B2 | 11/2012 | Cowan et al. | |
| 8,315,708 B2 | 11/2012 | Berthelsdorf et al. | |
| 8,321,021 B2 | 11/2012 | Kisker et al. | |
| 8,321,036 B2 | 11/2012 | Brockway et al. | |
| 8,332,036 B2 | 12/2012 | Hastings et al. | |
| 8,335,563 B2 | 12/2012 | Stessman | |
| 8,335,568 B2 | 12/2012 | Heruth et al. | |
| 8,340,750 B2 | 12/2012 | Prakash et al. | |
| 8,340,780 B2 | 12/2012 | Hastings et al. | |
| 8,352,025 B2 | 1/2013 | Jacobson | |
| 8,352,028 B2 | 1/2013 | Wenger | |
| 8,352,038 B2 | 1/2013 | Mao et al. | |
| 8,359,098 B2 | 1/2013 | Lund et al. | |
| 8,364,276 B2 | 1/2013 | Willis | |
| 8,369,959 B2 | 2/2013 | Meskens | |
| 8,369,962 B2 | 2/2013 | Abrahamson | |
| 8,380,320 B2 | 2/2013 | Spital | |
| 8,386,051 B2 | 2/2013 | Rys | |
| 8,391,981 B2 | 3/2013 | Mosesov | |
| 8,391,990 B2 | 3/2013 | Smith et al. | |
| 8,406,874 B2 | 3/2013 | Liu et al. | |
| 8,406,886 B2 | 3/2013 | Gaunt et al. | |
| 8,412,352 B2 | 4/2013 | Griswold et al. | |
| 8,417,340 B2 | 4/2013 | Goossen | |
| 8,417,341 B2 | 4/2013 | Freeberg | |
| 8,423,149 B2 | 4/2013 | Hennig | |
| 8,428,722 B2 | 4/2013 | Verhoef et al. | |
| 8,433,402 B2 | 4/2013 | Ruben et al. | |
| 8,433,409 B2 | 4/2013 | Johnson et al. | |
| 8,433,420 B2 | 4/2013 | Bange et al. | |
| 8,447,412 B2 | 5/2013 | Dal Molin et al. | |
| 8,452,413 B2 | 5/2013 | Young et al. | |
| 8,457,740 B2 | 6/2013 | Osche | |
| 8,457,742 B2 | 6/2013 | Jacobson | |
| 8,457,761 B2 | 6/2013 | Wariar | |
| 8,478,407 B2 | 7/2013 | Demmer et al. | |
| 8,478,408 B2 | 7/2013 | Hastings et al. | |
| 8,478,431 B2 | 7/2013 | Griswold et al. | |
| 8,504,156 B2 | 8/2013 | Bonner et al. | |
| 8,509,910 B2 | 8/2013 | Sowder et al. | |
| 8,515,559 B2 | 8/2013 | Roberts et al. | |
| 8,527,068 B2 | 9/2013 | Ostroff | |
| 8,532,790 B2 | 9/2013 | Griswold | |
| 8,541,131 B2 | 9/2013 | Lund et al. | |
| 8,543,205 B2 | 9/2013 | Ostroff | |
| 8,547,248 B2 | 10/2013 | Zdeblick et al. | |
| 8,548,605 B2 | 10/2013 | Ollivier | |
| 8,554,333 B2 | 10/2013 | Wu et al. | |
| 8,565,882 B2 | 10/2013 | Matos | |
| 8,565,897 B2 | 10/2013 | Regnier et al. | |
| 8,571,678 B2 | 10/2013 | Wang | |
| 8,577,327 B2 | 11/2013 | Makdissi et al. | |
| 8,588,926 B2 | 11/2013 | Moore et al. | |
| 8,612,002 B2 | 12/2013 | Faltys et al. | |
| 8,615,310 B2 | 12/2013 | Khairkhahan et al. | |
| 8,626,294 B2 | 1/2014 | Sheldon et al. | |
| 8,634,908 B2 | 1/2014 | Cowan | |
| 8,634,912 B2 | 1/2014 | Bornzin et al. | |
| 8,634,919 B1 | 1/2014 | Hou et al. | |
| 8,639,335 B2 | 1/2014 | Peichel et al. | |
| 8,644,934 B2 | 2/2014 | Hastings et al. | |
| 8,649,859 B2 | 2/2014 | Smith et al. | |
| 8,670,842 B1 | 3/2014 | Bornzin et al. | |
| 8,676,319 B2 | 3/2014 | Knoll | |
| 8,676,335 B2 | 3/2014 | Katoozi et al. | |
| 8,700,173 B2 | 4/2014 | Edlund | |
| 8,700,181 B2 | 4/2014 | Bornzin et al. | |
| 8,705,599 B2 | 4/2014 | dal Molin et al. | |
| 8,718,773 B2 | 5/2014 | Willis et al. | |
| 8,738,147 B2 | 5/2014 | Hastings et al. | |
| 8,744,572 B1 | 6/2014 | Greenhut et al. | |
| 8,747,314 B2 | 6/2014 | Stahmann et al. | |
| 8,755,884 B2 | 6/2014 | Demmer et al. | |
| 8,758,365 B2 | 6/2014 | Bonner et al. | |
| 8,774,572 B2 | 7/2014 | Hamamoto | |
| 8,781,605 B2 | 7/2014 | Bornzin et al. | |
| 8,788,035 B2 | 7/2014 | Jacobson | |
| 8,788,053 B2 | 7/2014 | Jacobson | |
| 8,798,740 B2 | 8/2014 | Samade et al. | |
| 8,798,745 B2 | 8/2014 | Jacobson | |
| 8,798,762 B2 | 8/2014 | Fain et al. | |
| 8,798,770 B2 | 8/2014 | Reddy | |
| 8,805,505 B1 | 8/2014 | Roberts | |
| 8,805,528 B2 | 8/2014 | Corndorf | |
| 8,812,109 B2 | 8/2014 | Blomqvist et al. | |
| 8,818,504 B2 | 8/2014 | Bodner et al. | |
| 8,831,747 B1 | 9/2014 | Min et al. | |
| 8,855,789 B2 | 10/2014 | Jacobson | |
| 8,868,186 B2 | 10/2014 | Kroll | |
| 8,886,339 B2 | 11/2014 | Faltys et al. | |
| 8,903,500 B2 | 12/2014 | Smith et al. | |
| 8,903,513 B2 | 12/2014 | Ollivier | |
| 8,914,131 B2 | 12/2014 | Bornzin et al. | |
| 8,923,795 B2 | 12/2014 | Makdissi et al. | |
| 8,923,963 B2 | 12/2014 | Bonner et al. | |
| 8,938,300 B2 | 1/2015 | Rosero | |
| 8,942,806 B2 | 1/2015 | Sheldon et al. | |
| 8,954,030 B1* | 2/2015 | Buchheit | A61N 1/3925 455/404.1 |
| 8,958,892 B2 | 2/2015 | Khairkhahan et al. | |
| 8,977,358 B2 | 3/2015 | Ewert et al. | |
| 8,989,873 B2 | 3/2015 | Locsin | |
| 8,996,109 B2 | 3/2015 | Karst et al. | |
| 9,002,467 B2* | 4/2015 | Smith | A61N 1/372 607/32 |
| 9,008,776 B2 | 4/2015 | Cowan et al. | |
| 9,008,777 B2 | 4/2015 | Dianaty et al. | |
| 9,014,818 B2 | 4/2015 | Deterre et al. | |
| 9,017,341 B2 | 4/2015 | Bornzin et al. | |
| 9,020,611 B2 | 4/2015 | Khairkhahan et al. | |
| 9,037,262 B2 | 5/2015 | Regnier et al. | |
| 9,042,984 B2 | 5/2015 | Demmer et al. | |
| 9,072,911 B2 | 7/2015 | Hastings et al. | |
| 9,072,913 B2 | 7/2015 | Jacobson | |
| 9,155,882 B2 | 10/2015 | Grubac et al. | |
| 9,168,372 B2 | 10/2015 | Fain | |
| 9,168,380 B1 | 10/2015 | Greenhut et al. | |
| 9,168,383 B2* | 10/2015 | Jacobson | A61N 1/368 |
| 9,180,285 B2 | 11/2015 | Moore et al. | |
| 9,192,774 B2 | 11/2015 | Jacobson | |
| 9,205,225 B2 | 12/2015 | Khairkhahan et al. | |
| 9,216,285 B1 | 12/2015 | Boling et al. | |
| 9,216,293 B2 | 12/2015 | Berthiaume et al. | |
| 9,216,298 B2 | 12/2015 | Jacobson | |
| 9,227,077 B2 | 1/2016 | Jacobson | |
| 9,238,144 B2* | 1/2016 | Greene | A61N 1/37252 |
| 9,238,145 B2 | 1/2016 | Wenzel et al. | |
| 9,242,102 B2 | 1/2016 | Khairkhahan et al. | |
| 9,242,113 B2 | 1/2016 | Smith et al. | |
| 9,248,300 B2 | 2/2016 | Rys et al. | |
| 9,265,436 B2 | 2/2016 | Min et al. | |
| 9,265,962 B2 | 2/2016 | Dianaty et al. | |
| 9,278,218 B2 | 3/2016 | Karst et al. | |
| 9,278,229 B1 | 3/2016 | Reinke et al. | |
| 9,283,381 B2 | 3/2016 | Grubac et al. | |
| 9,283,382 B2 | 3/2016 | Berthiaume et al. | |
| 9,289,612 B1 | 3/2016 | Sambelashvili et al. | |
| 9,302,115 B2 | 4/2016 | Molin et al. | |
| 9,333,364 B2 | 5/2016 | Echt et al. | |
| 9,370,663 B2 | 6/2016 | Moulder | |
| 9,375,580 B2 | 6/2016 | Bonner et al. | |
| 9,375,581 B2 | 6/2016 | Baru et al. | |
| 9,656,091 B2* | 5/2017 | Huelskamp | A61B 5/0452 |
| 9,724,522 B2* | 8/2017 | Stahmann | A61N 1/37288 |
| 9,853,743 B2* | 12/2017 | Schmidt | H04B 13/005 |

(56) References Cited

U.S. PATENT DOCUMENTS

| | | |
|---|---|---|
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0041866 A1 | 3/2003 | Linberg et al. |
| 2003/0088278 A1 | 5/2003 | Bardy et al. |
| 2003/0097153 A1 | 5/2003 | Bardy et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1* | 7/2004 | Amundson ........ A61N 1/37252 607/60 |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2006/0040707 A1* | 2/2006 | Kish ........ H04B 7/061 455/562.1 |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1* | 10/2006 | Markowitz ............ A61N 1/025 607/5 |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0027508 A1 | 2/2007 | Cowan |
| 2007/0049992 A1 | 3/2007 | Freeberg |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255330 A1* | 11/2007 | Lee ............... A61N 1/37288 607/32 |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154322 A1 | 6/2008 | Jackson et al. |
| 2008/0177194 A1* | 7/2008 | Zhang ............... A61N 1/365 600/513 |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |

(56) References Cited

U.S. PATENT DOCUMENTS

| | | |
|---|---|---|
| 2009/0171414 A1 | 7/2009 | Kelly et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0125281 A1 | 5/2010 | Jacobson et al. |
| 2010/0168761 A1 | 7/2010 | Kassab et al. |
| 2010/0168819 A1* | 7/2010 | Freeberg ............ A61N 1/37252 607/60 |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1* | 7/2011 | Kivi ............ A61N 1/37276 607/60 |
| 2011/0190835 A1* | 8/2011 | Brockway ............ A61N 1/39 607/6 |
| 2011/0208260 A1 | 8/2011 | Jacobson |
| 2011/0218587 A1 | 9/2011 | Jacobson |
| 2011/0230734 A1* | 9/2011 | Fain ............ A61N 1/37211 600/302 |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2011/0313493 A1* | 12/2011 | Keenan ............ A61B 5/0031 607/60 |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1* | 3/2012 | Fontaine ............ A61N 1/37 607/60 |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0109260 A1* | 5/2012 | Stancer ............ A61N 1/3718 607/60 |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1* | 7/2012 | Berg ............ A61N 1/3925 607/5 |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1* | 11/2012 | Greenhut ............ A61B 5/02108 600/485 |
| 2012/0277606 A1 | 11/2012 | Ellingson et al. |
| 2012/0283795 A1* | 11/2012 | Stancer ............ A61N 1/3688 607/11 |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1* | 4/2013 | Martin ............ G06F 19/322 607/60 |
| 2013/0103047 A1 | 4/2013 | Steingisser et al. |
| 2013/0103109 A1 | 4/2013 | Jacobson |
| 2013/0110008 A1* | 5/2013 | Bourget ............ A61B 5/11 600/595 |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0234861 A1* | 9/2013 | Abrahamson ...... A61N 1/37223 340/870.02 |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |

(56) References Cited

U.S. PATENT DOCUMENTS

| | | |
|---|---|---|
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268028 A1* | 10/2013 | Trier .................. A61N 1/37229 607/60 |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0257324 A1 | 9/2014 | Fain |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0038742 A1* | 2/2016 | Stahmann .............. A61N 1/371 607/28 |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2017/0007129 A1* | 1/2017 | Kaib .................... A61B 5/0022 |
| 2017/0216611 A1* | 8/2017 | Yoder ................ A61N 1/37217 |
| 2017/0281961 A1* | 10/2017 | Stahmann .............. A61N 1/371 |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2818200 A1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |

(56) References Cited

FOREIGN PATENT DOCUMENTS

| WO | 2013080038 A2 | 6/2013 |
| WO | 2013098644 A3 | 8/2013 |
| WO | 2013184787 A1 | 12/2013 |

OTHER PUBLICATIONS

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Wegmüller, "Intra-Body Communication for Biomedical Sensor Networks," Diss. ETH, No. 17323, 1-173, 2007.

Spickler et al., "Totally Self-Contained Intracardiac Pacemaker," Journal of Electrocardiology, vol. 3(3&4): 324-331, 1970.

"Instructions for Use System 1, Leadless Cardiac Pacemaker (LCP) and Delivery Catheter," Nanostim Leadless Pacemakers, pp. 1-28, 2013.

\* cited by examiner

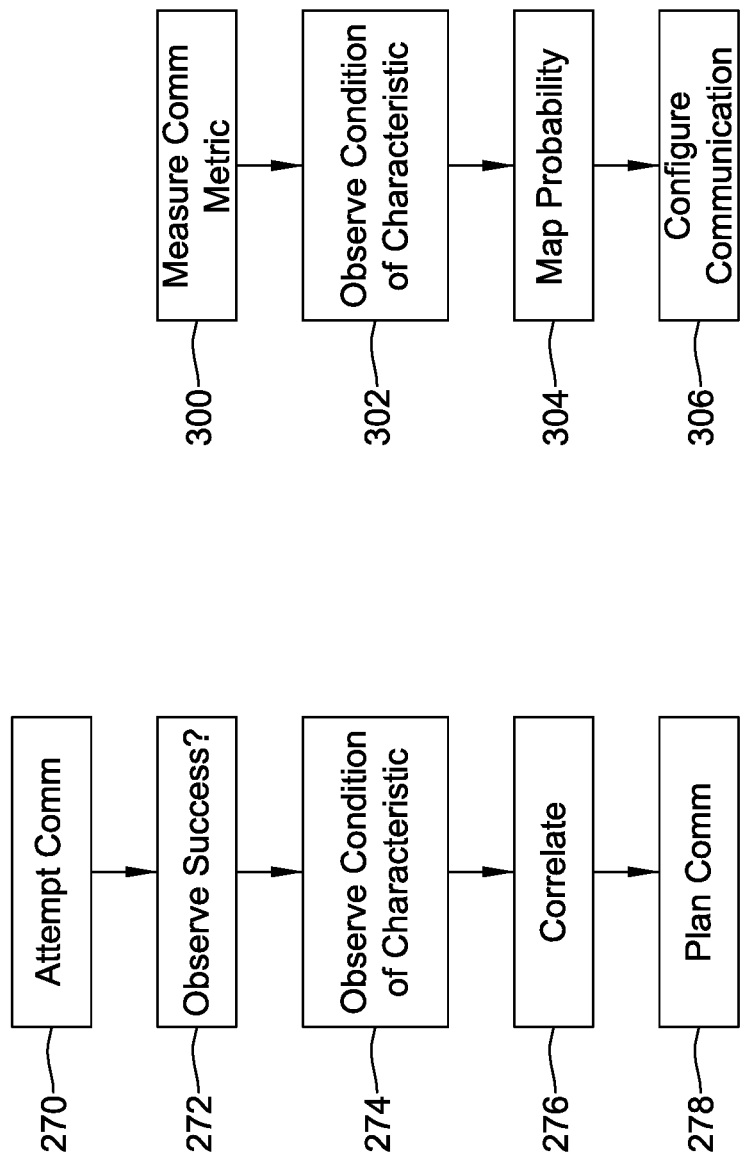

COMMUNICATIONS IN A MEDICAL DEVICE SYSTEM WITH TEMPORAL OPTIMIZATION

CROSS REFERENCE TO RELATED APPLICATIONS

The present application claims the benefit of and priority to U.S. Provisional Patent Application No. 62/134,752, filed Mar. 18, 2015, titled COMMUNICATIONS IN A MEDICAL DEVICE SYSTEM WITH TEMPORAL OPTIMIZATION, the disclosure of which is incorporated herein by reference.

TECHNICAL FIELD

The present disclosure generally relates to medical devices, and more particularly to communications between medical devices in a multi-device system.

BACKGROUND

Various active implantable devices are available or in development for treating and/or diagnosing numerous ailments. Some examples include cardiac assist devices, pacemakers, defibrillators, cardiac monitors, neurostimulation and neuromodulation systems, drug and medication pumps, and others. A patient may have multiple implanted devices and may benefit in some circumstances by enabling such devices to communicate with one another. Because these implantable devices are often reliant on battery power, communication between devices should be designed for efficiency and to limit power consumption.

SUMMARY

The present disclosure relates generally to systems and methods for managing communication strategies with temporal optimization relative to one or more identified conditions in the body.

A first example is a first medical device comprising: means for communicating with a second implantable medical device; means for identifying a first characteristic having a possible impact on communication success; means for selecting a first condition of the first characteristic on which to trigger an attempt at communication; means for determining that the first condition of the first characteristic is present and attempting communication with the second implantable medical device; means for assessing whether the attempted communication was successful; and means for associating the first condition and first characteristic with a reduced likelihood of communication success if the attempted communication was not successful.

A second example takes the form of the first medical device of the first example wherein the means for communicating is configured for communication by conducted communication. A third example takes the form of a first medical device as in either of the first two examples wherein the first medical device is configured as an implantable medical device. A fourth example takes the form of a first medical device of any of the first three example, further comprising means for associating the first condition and first characteristic with an improved likelihood of communication success if the attempted communication was successful.

A fifth example takes the form of a first medical device of any of the first four examples further comprising optimization means for selecting multiple conditions of the first characteristic and repeatedly operating the means for determining, means for assessing and means for associating for each of multiple conditions of the first characteristic to determine whether the first characteristic can be used to determine a likelihood of communication success.

A sixth example takes the form of a first medical device of any of the first to fifth examples further comprising means for identifying a second characteristic, wherein the means for determining, means for assessing and means for assessing are operable to test at least a first condition of the second characteristic to determine whether the second characteristic can be used to determine a likelihood of communication success.

A seventh example takes the form of a first medical device of any of the first to sixth examples wherein the first characteristic is a detected status of a cardiac cycle, and the first condition is the occurrence of one of a cardiac R-wave or a cardiac T-wave. An eighth example takes the form of a first medical device of any of the first to sixth examples wherein the first characteristic is a detected status of a cardiac cycle, and the first condition is the occurrence of a pacing pulse. A ninth example takes the form of a first medical device of any of the first to sixth examples wherein the first characteristic is a detected status of a respiration cycle, and the first condition is the occurrence of one of an exhale or an inhale. A tenth example takes the form of a first medical device of any of the first to sixth examples wherein the first characteristic is a detected a transthoracic impedance, and the first condition is the occurrence of one of a maximum impedance or a minimum impedance. An eleventh example takes the form of a first medical device of any of the first to sixth examples wherein the first characteristic is a cyclic biological phenomenon and the first condition is the occurrence of a recurring event in the cyclic biological phenomenon.

A twelfth example takes the form of an implantable medical device system comprising a first medical device as of any of the first to eleventh examples and a second implantable medical device configured for communication with the first medical device, wherein the first medical device is an intracardiac pacing device, and the second implantable medical device is a subcutaneous defibrillator.

A thirteenth example takes the form of an implantable medical device system comprising a first medical device as in any of the first to eleventh examples, and a second implantable medical device configured for communication with the first medical device, wherein the first medical device is a subcutaneous defibrillator, and the second implantable medical device is an intracardiac pacing device.

A fourteenth example is a first medical device comprising means for communicating with a second medical device; means for determining a first condition of a first characteristic is present; and means for modifying communication with the second implantable medical device based on the determination; wherein at least one of the first and second medical devices is implantable. A fifteenth example takes the form of a first medical device as in the fourteenth example wherein the first characteristic is a cyclic biological phenomenon and the first condition is the occurrence of a recurring event in the cyclic biological phenomenon.

A sixteenth example is a first medical device comprising a communication module for communicating with a second implantable medical device and a controller operatively coupled to the communication module for at least one of receiving or transmitting messages, the controller configured to optimize communication by: identifying a first characteristic having a possible impact on communication success;

selecting a first condition of the first characteristic on which to trigger an attempt at communication; determining that the first condition of the first characteristic is present and attempting communication with the second implantable medical device; assessing whether the attempted communication was successful; and if the attempted communication was not successful, associating the first condition and first characteristic with a reduced likelihood of communication success.

A seventeenth example takes the form of the first medical device of the sixteenth example wherein the communication module is configured for communication by conducted communication. An eighteenth example takes the form of the first medical device of either the sixteenth or seventeenth examples wherein the first medical device is configured as an implantable medical device. A nineteenth example takes the form of the first medical device of any of the sixteenth to eighteenth examples, wherein the controller is further configured to associate the first condition and first characteristic with an improved likelihood of communication success if the attempted communication was successful. A twentieth example takes the form of the first medical device of any of the sixteenth to nineteenth examples, wherein the controller is configured to further optimize communication by selecting multiple conditions of the first characteristic and repeating the determining and assessing steps for each of multiple conditions of the first characteristic to determine whether the first characteristic can be used to determine a likelihood of communication success. A twenty-first example takes the form of the first medical device of any of the sixteenth to twentieth examples, wherein the controller is configured to identify a second characteristic and test at least a first condition of the second characteristic to determine whether the second characteristic can be used to determine a likelihood of communication success.

A twenty-second example takes the form of the first medical device of any of the sixteenth to twenty-first examples wherein the first characteristic is a detected status of a cardiac cycle, and the first condition is the occurrence of one of a cardiac R-wave or a cardiac T-wave. A twenty-third example takes the form of the first medical device of any of the sixteenth to twenty-first examples wherein the first characteristic is a detected status of a cardiac cycle, and the first condition is the occurrence of a pacing pulse. A twenty-fourth examples takes the form of the first medical device of any of the sixteenth to twenty-first examples wherein the first characteristic is a detected status of a respiration cycle, and the first condition is the occurrence of one of an exhale or an inhale. A twenty-fifth example takes the form of the first medical device of any of the sixteenth to twenty-first examples wherein the first characteristic is a detected a transthoracic impedance, and the first condition is the occurrence of one of a maximum impedance or a minimum impedance. A twenty-sixth examples takes the form of the first medical device of any of the sixteenth to twenty-first examples wherein the first characteristic is a cyclic biological phenomenon and the first condition is the occurrence of a recurring event in the cyclic biological phenomenon.

A twenty-seventh example takes the form of an implantable medical device system comprising a first medical device as in any of the sixteenth to twenty-sixth examples and a second implantable medical device configured for communication with the first medical device, wherein the first medical device is an intracardiac pacing device, and the second medical device is a subcutaneous defibrillator. A twenty-eighth example takes the form of an implantable medical device system comprising a first medical device as in any of the sixteenth to twenty-sixth examples, and a second implantable medical device configured for communication with the first medical device, wherein the first medical device is a subcutaneous defibrillator, and the second implantable medical device is an intracardiac pacing device.

A twenty-ninth example is a first medical device comprising a communication module for communicating with a second medical device and a controller operatively coupled to the communication module messages, the controller configured to optimize communication by: determining a first condition of a first characteristic is present; and modifying communication with the second implantable medical device based on the determination; wherein at least one of the first and second medical devices is implantable.

A thirtieth example takes the form of the first medical device of the twenty-ninth example wherein the first characteristic is a cyclic biological phenomenon and the first condition is the occurrence of a recurring event in the cyclic biological phenomenon. A thirty-first example takes the form of the first medical device of the thirtieth example wherein the cyclic biological phenomenon is one of a respiration cycle or a cardiac cycle.

A thirty-second example is a method of communication with an implantable medical device comprising: identifying a characteristic having a possible impact on communication success; selecting a condition of the characteristic on which to trigger an attempt at communication; attempting communication based on the condition of the characteristic occurring; and assessing whether the communication was likely successful.

A thirty-third example takes the form of a method as in the thirty-second example, further comprising: if the communication was successful, associating the characteristic and condition with an improved likelihood of communication success; or if the communication was not successful, associating the characteristic and condition with a reduced likelihood of communication success.

A thirty-fourth example takes the form of a method as in either of the thirty-second or thirty-third examples wherein the characteristic is a cyclic biological phenomenon and the condition is the occurrence of a recurring event in the cyclic biological phenomenon. A thirty-fifth example takes the form of a method as in the thirty-fourth example wherein the cyclic biological phenomenon is one of a respiration cycle or a cardiac cycle.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which:

FIGS. 7-11 are flow diagrams of a several illustrative methods that may be implemented by a medical device or medical device system.

Figure 1:
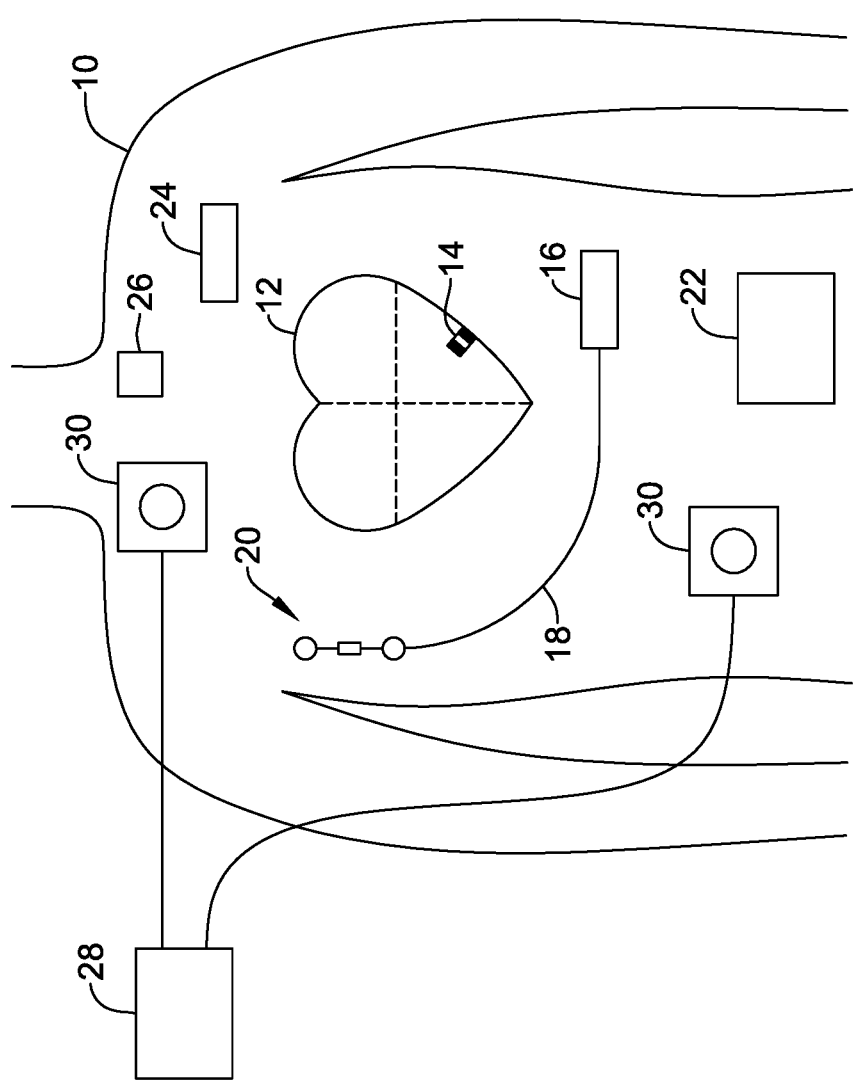
FIG. 1 illustrates a patient having a plurality of implantable medical devices.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

FIG. 1 illustrates a patient having a plurality of implantable medical devices. A patient, 10 is shown having a leadless cardiac pacemaker (LCP) 14 implanted inside the heart 12. A subcutaneous implantable defibrillator (SICD) 16 having a left axillary canister and lead 18 extending to electrodes 20 is also shown. The patient may also have an insulin pump 22, a pain pump 24 for delivering pain medication to the shoulder, and/or a nerve stimulator 26 having a lead (not shown) extending to the neck or head.

Other devices could be substituted for those shown in FIG. 1, and the positions shown for each device are not intended to be limiting. Some additional or alternative examples include other pacemakers or defibrillators such as those with transvenous, intracardiac, epicardial, or substernal leads and/or electrodes, a cardiac monitor, left ventricular assist device, spinal cord stimulator, vagus nerve stimulator, gastric electric stimulator, sacral nerve stimulator, and/or any other implantable medical device.

In some embodiments an implanted device may be in communication with one or more extracorporeal devices. The extracorporeal device(s) may be affixed to the patient in a wearable configuration. The extracorporeal device(s) may provide a therapy, for example a nerve stimulation therapy, muscle simulation therapy and/or respiration therapy (e.g. continuation positive airway pressure therapy). Additionally or alternatively the extracorporeal device may provide a diagnostic function, for example a cardiac monitoring function or/and a respiratory monitoring function. Additionally or alternatively the extracorporeal device may serve as a communication link between an implanted device and a device not in physical contact with the patient (i.e. remote from the body). In some embodiments one or more parts/elements of a device or system may be implanted and other portions may be extracorporeal (e.g. a drug pump or a continuous glucose monitor).

These various systems may be interrogated by an external device or a "programmer" 28, which may optionally use one or more skin electrodes 30 to assist with communication to an implanted device. Skin electrodes 30 may be used for conducted communication with an implantable device. Conducted communication is communication via electrical signals which propagate via patient tissue and are generated by more or less ordinary electrodes. By using the existing electrodes, conducted communication does not rely on an antenna and an oscillator/resonant circuit having a tuned center frequency common to both transmitter and receiver.

For other communication approaches such as RF or inductive communication, the programmer 28 may instead use a programming wand or may have an antenna integral with the programmer 28 housing for communication. Though not shown in detail, the programmer 28 may include any suitable user interface, including a screen, buttons, keyboard, touchscreen, speakers, and various other features widely known in the art.

It is unlikely a single patient 10 would have all of the different systems implanted as shown in FIG. 1. For purposes of the present invention, it is assumed that a patient may have at least two implantable systems simultaneously, and it may be beneficial to facilitate communication between the at least two implantable systems. The mode for communication between two implanted systems may be conducted communication, though other approaches (optical, acoustic, inductive or RF, for example) could be used instead.

Figure 2:
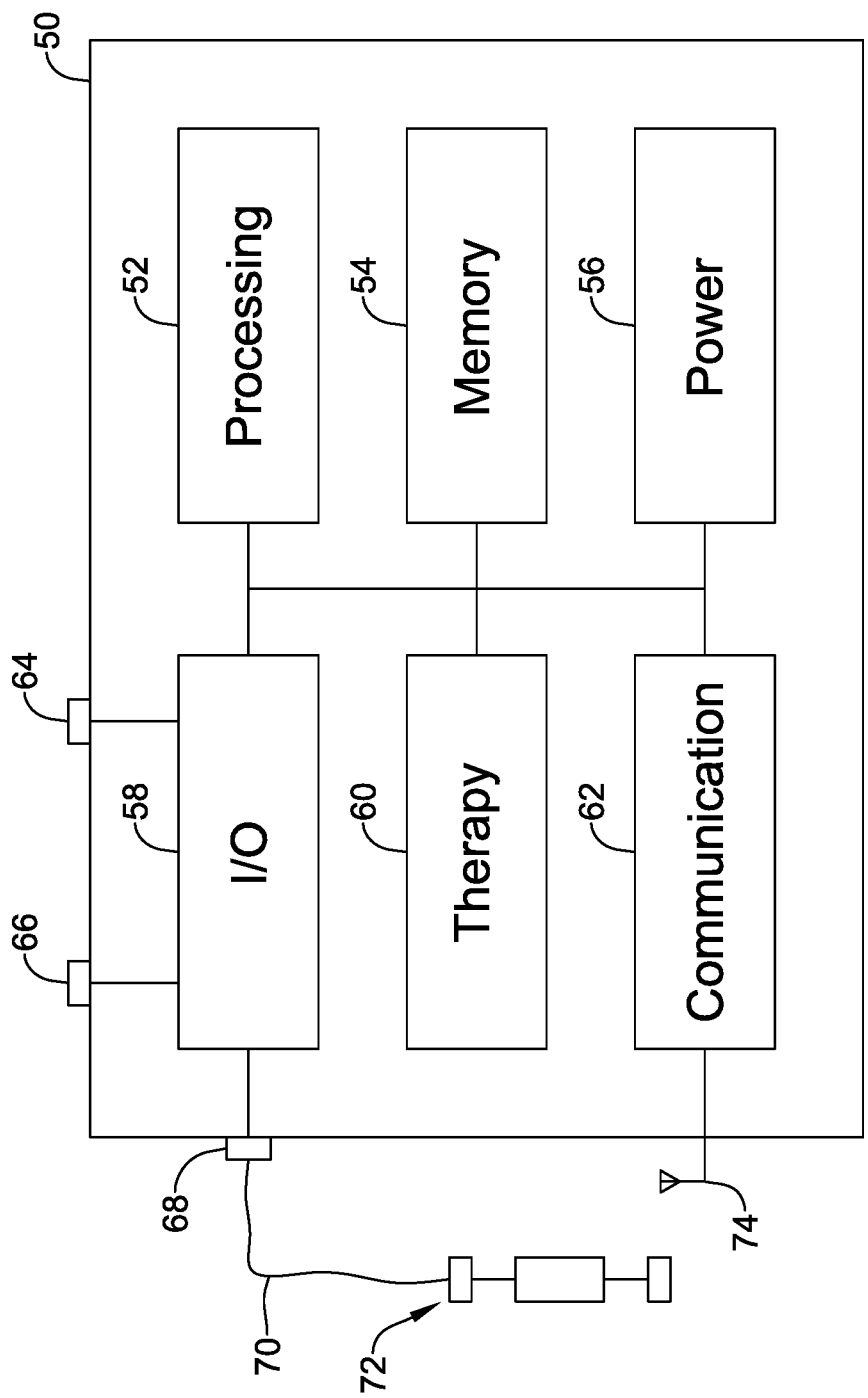
FIG. 2 illustrates a block diagram of an implantable medical device.

FIG. 2 illustrates a block diagram of an implantable medical device. The illustration indicates various functional blocks within a device 50, including a processing block 52, memory 54, power supply 56, input/output circuitry 58, therapy circuitry 60, and communication circuitry 62. The I/O circuitry 58 can be coupled to one or more electrodes 64, 66 on the device 50 housing, and may also couple to a header 68 for attachment to one or more leads 70 having additional electrodes 72. The communication circuitry 62 may be coupled to an antenna 74 for radio communication (such as Medradio, ISM, or other RF) and/or may couple via the I/O circuitry 58 to a combination of electrodes 64, 66, 72, for conducted communication.

The processing block 52 will generally control operations in the device 50 and may include a microprocessor or microcontroller and/or other circuitry and logic suitable to its purpose. Processing block 52 may include dedicated circuits or logic for device functions such as converting analog signals to digital data, processing digital signals, detecting events in a biological signal, etc. The memory block may include RAM, ROM, flash and/or other memory circuits for storing device parameters, programming code, and data related to the use, status, and history of the device 50. The power supply 56 typically includes one to several batteries, which may or may not be rechargeable depending on the device 50. For rechargeable systems there would additionally be charging circuitry for the battery (not shown).

The I/O circuitry 58 may include various switches or multiplexers for selecting inputs and outputs for use. I/O circuitry 58 may also include filtering circuitry and amplifiers for pre-processing input signals. In some applications the I/O circuitry will include an H-Bridge to facilitate high power outputs, though other circuit designs may also be used. Therapy block 60 may include capacitors and charging circuits, modulators, and frequency generators for providing electrical outputs. For devices such as insulin and drug pumps the therapy circuit 60 may include a pump or pump actuator coupled to a delivery system for outputting therapeutic material, rather than using the I/O circuitry 58 as would be typical for systems that generate an electrical therapy output.

Communications circuitry 62 may include a frequency generator/oscillator and mixer for creating output signals to transmit via the antenna 74. Some devices 50 may include a separate ASIC for the communications circuitry 62, for example. For devices using an inductive communication output, an inductive coil may be included. Devices may also use optical or acoustic communication approaches, and suitable circuits, transducers, generators and receivers may be included for these modes of communication as well or instead of those discussed above.

As those skilled in the art will understand, additional circuits may be provided beyond those shown in FIG. 2. For example, some devices 50 may include a Reed switch or other magnetically reactive element to facilitate magnet wakeup or reset of the device by a user. Some systems may omit one or more blocks, for example, an implantable cardiac monitor can omit therapy block 60, and an LCP may exclude the header 68 for coupling to lead 70.

In several embodiments, the present invention is directed toward the management and optimization of conducted communication between two implanted medical devices. For example, an LCP may communicate with an SICD. The LCP may, for example, provide a detected heartbeat rate to the SICD in order to assist the SICD in making a therapy determination. In another example, the SICD may request status from the LCP or may direct the LCP to deliver pacing pulses.

Other combinations of systems may use conducted communication between devices for various reasons. For example, if a patient has both a drug pump and a spinal cord stimulator, the drug pump may communicate to the spinal cord stimulator that it is in need of servicing, such that both systems may use their internal annunciating mechanisms to alert the patient that the drug pump requires service. As integrated systems develop, it may become possible to develop simplified devices that omit, for example, standard telemetry or annunciator circuits, and instead use conducted communication to another device that includes full telemetry and annunciator circuits. If telemetry and/or annunciator circuits are omitted in one or more devices, the devices may become smaller and power consumption may be reduced. Thus conducted communication optimization may facilitate development of smaller and/or longer lasting devices in addition to facilitating inter-device coordination for therapy purposes.

FIGS. 3-6 are schematic diagrams illustrating communications packets relative to biological signals. Conducted communication taking place within the body is subject to interference from various biological functions. Respiration and the cardiac cycle are two particular cyclic biological functions of interest, though any other biological function, cyclic or not, may also be addressed using the methods and devices herein.

Figure 3:
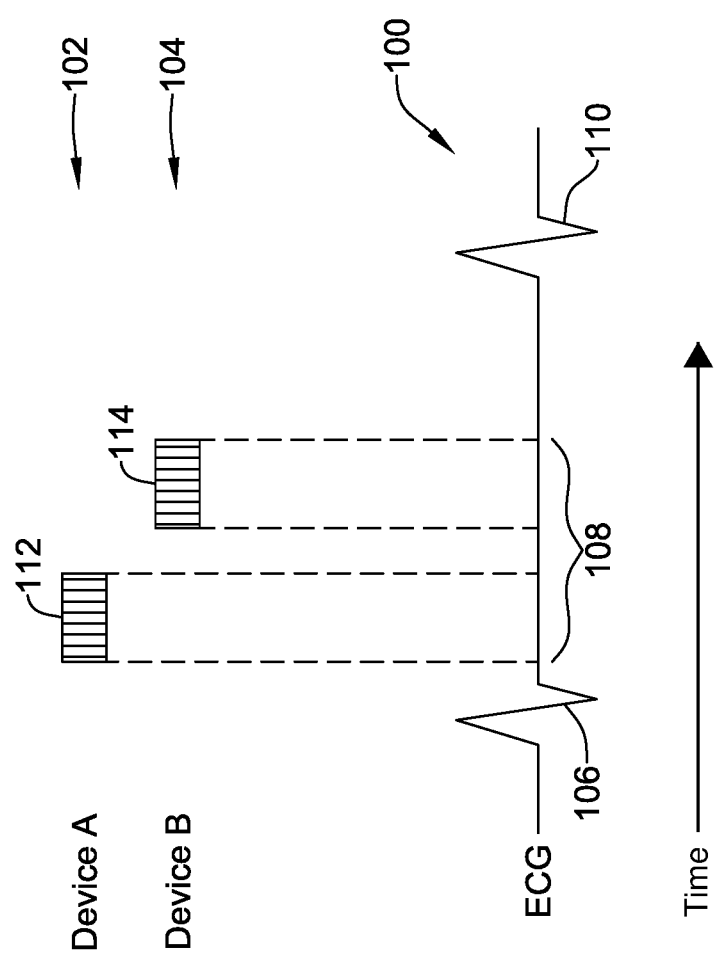
FIGS. 3-6 are schematic diagrams illustrating communications pulses relative to biological signals.

FIG. 3 illustrates an ECG signal at 100, and communications by Device A at 102 and Device B at 104. The ECG shows a QRS complex (a heartbeat) at 106 followed by an interval 108, and another beat at 110. In this illustration, Device A sends a data packet 112 during the interval 108 between beats 106, 110, and Device B responds with a packet at 114 during the same interval 108. In another embodiment, Device B may respond after the subsequent beat at 110.

The phrase "data packet" is used for convenience and should be understood as generically including any type of message sent from one device to another. No particular message/frame structure, type of data, size or other meaning should be implied.

Figure 4:
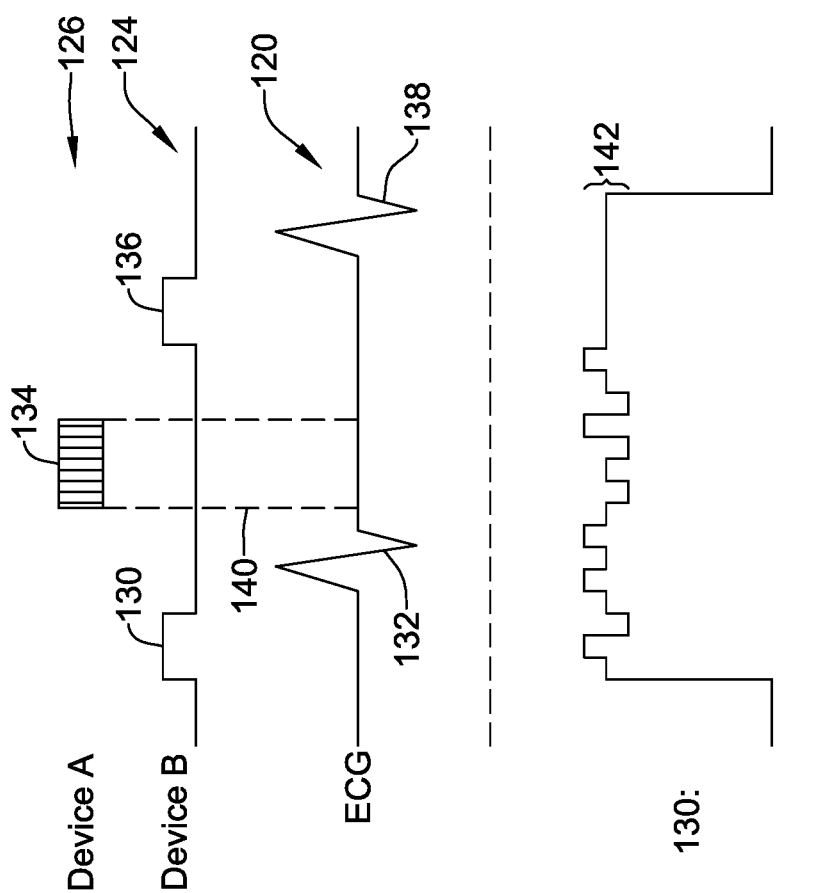

In FIG. 3, the data packets are shown as being sent independent of therapy output by either Device A or Device B. FIG. 4 shows a scheme in which Device B is configured to embed communications in a therapy output. The ECG is shown at 120, and the therapy output of Device B is shown at 124, while the communications from Device A are shown at 126. The therapy output 124 includes pacing pulses 130 and 136, which trigger beats 132 and 138 respectively on the ECG 120.

A detail view of pacing pulse 130 is shown below, and it is seen at 142 that the shape of the pacing pulse 130 includes amplitude modulation embedding a data packet. Other approaches to embedding information in a pacing pulse can be used; the illustration is simplified in FIG. 4 since the present invention is not limited to embedding data in a therapy output nor is it limited to communicating via therapy output-encoded data. Preferably, the embedded data 142 does not affect the effectiveness of therapy of the pacing pulse 130.

Device A is designed to recognize the data 142 embedded in the pacing pulse 130. In this example, Device A responds with a data packet after some delay such that data packet 134 follows the end of the QRS complex of beat 132. In an alternative, Device A could sent data packet 134 and Device B would respond with a message embedded in pacing pulse 136.

The signals for conducted communication are generally intended to have amplitudes that will not cause cardiac or skeletal muscle contraction, with the exception of the case in which the conducted communication is embedded in a stimulus signal, such as pacing pulse 130 with data 132. The patient should not be aware of the conducted communication signal.

In FIG. 4, the amplitude, duration and/or frequency content of the data packet 134 would be selected to avoid stimulating muscle (skeletal or cardiac). Delivery of the data packet 134 during the QRS complex 132 could cause Device B to miss the signal or interpret it as part of the QRS complex 132. Therefore, as indicated at 140, the data packet 134 is preferably delivered after the conclusion of the QRS complex for beat 132, and preferably ends before delivery of the next pacing pulse 136.

One approach to delivering data packet 134 would be to call for a fixed delay after the conclusion of the pacing pulse 130, such as a 300 millisecond delay allowing for the (typically wide) paced QRS complex for beat 132 to be finished. Another approach would be to sense the ECG 120 for termination of the QRS. Each approach has limitations, however. A fixed period may not account for other portions of the ECG, such as the T-wave and/or S-T segment, which can vary in amplitude between patients and even within a patient based on the patient's posture, activity level, etc. Detecting the end of the QRS can be highly dependent on the location of the electrodes used to sense the ECG 120. Moreover, it may be more effective if both Device A and Device B know when the data packet 134 is expected. Thus a temporal optimization may be highly useful to enhance communication reliability.

As used in the present disclosure, the ECG represents the electrical state of the patient's heart, and is a "characteristic" of the patient. The occurrence of a QRS complex, or other event, in the ECG represents a "condition" of the ECG characteristic. Other characteristics and conditions of characteristics are discussed below.

Figure 5:
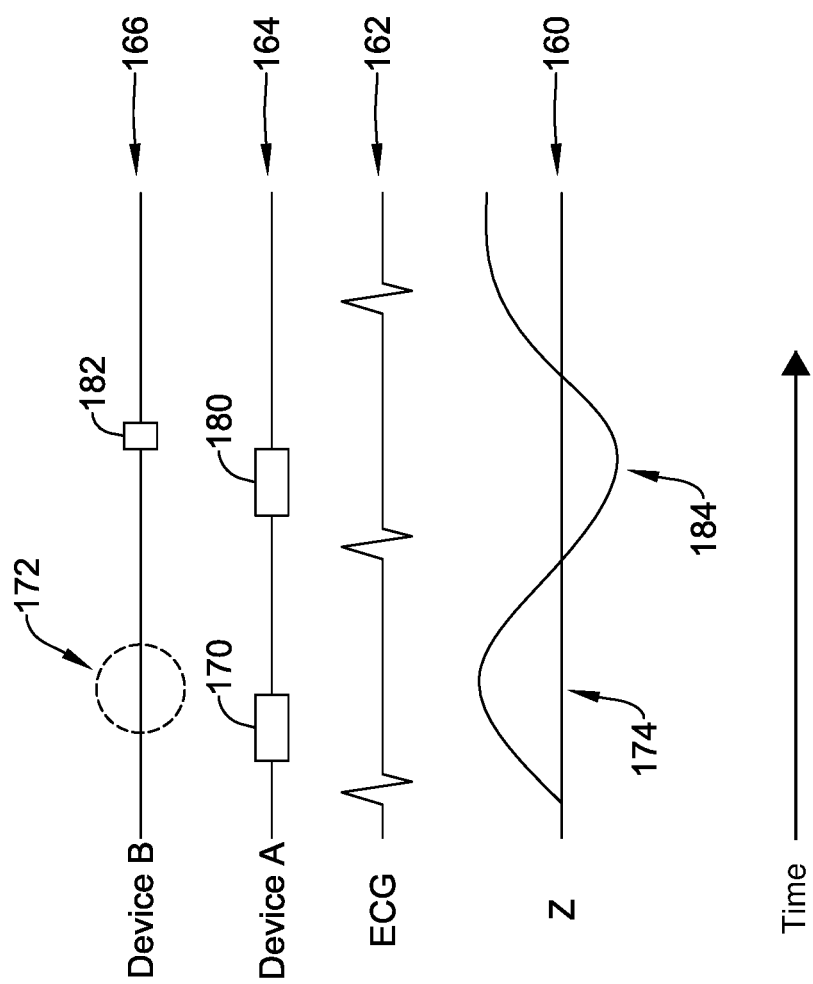

FIG. 5 illustrates another characteristic and an illustrative example of its use. Here, a transthoracic impedance is shown at 160, an ECG is shown at 162, and the communication packets for Device A and Device B are shown at 164 and 166, respectively. The transthoracic impedance 160 may vary with patient movement, such as respiration. In this sequence, the beats of the ECG are avoided by Device A when it sends out data packets 170 and 180. However, Device B fails to respond at 172 to data packet 170.

Reviewing the transthoracic impedance suggests that a high transthoracic impedance at 174 may have negatively affected communication of data packet 170. This may be treated as a "high condition" of the "characteristic" of transthoracic impedance.

As a result, in this embodiment, the method includes delivering the next packet 180, both outside of the QRS complex of ECG 162, but also at a point where the transthoracic impedance 160 is low as shown at 184. This time, the data packet 180 is received by device B, generating an acknowledgement or other responsive output at 182. Analysis of the observed characteristic (impedance), suggests that the condition of low transthoracic impedance at 184 may have positively impacted the success of data packet 180. The illustrative system may record one or both of the success and failure as indicating a likely connection between transthoracic impedance and communication success. Reviewing FIG. 5 alongside FIG. 4 shows that a temporal optimization may take into account multiple characteristics.

Figure 6:
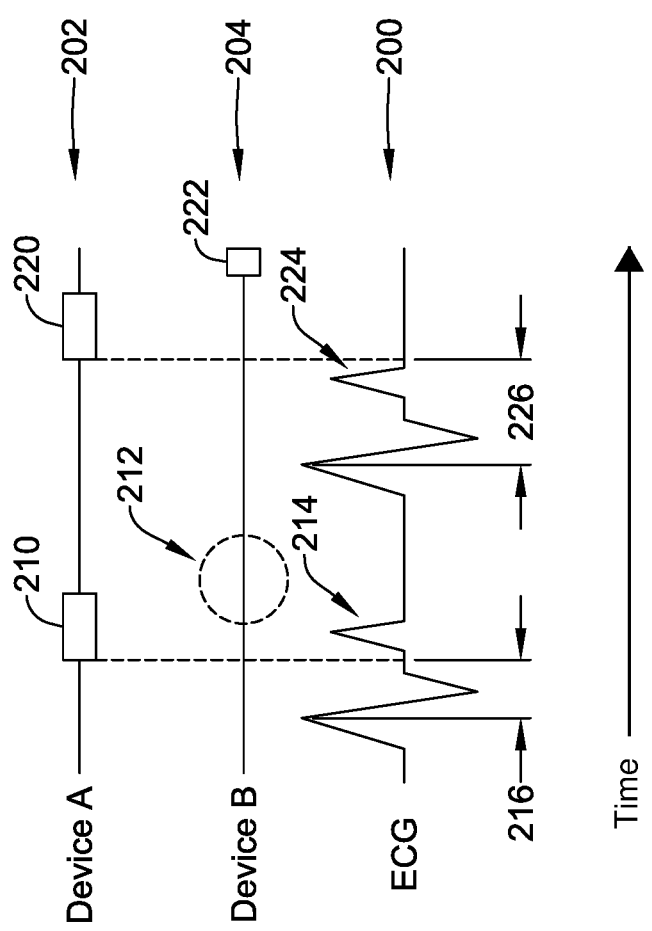

The QRS complex is not the only condition which may arise within the ECG characteristic; the T-wave and P-wave, for example, or S-T segment elevation, are also potential conditions that may impact communication success. In FIG. 6, the ECG is represented at 200, and communications activity of Devices A and B is shown at 202 and 204 respectively.

Device A attempts communication at 210, but the communication fails to be observed by Device B, which does not reply at 212 as expected. Closer review of the ECG 200 indicates that the QRS complex is followed by a prominent T-wave shown at 214. Either of Device A or Device B may assess the ECG and the failed communication attempt and identify a likely relationship, and make an adjustment to the timing of a later communication attempt.

In an alternative example, Device A may not identify whether there is a prominent T-wave; it simply knows that the communication attempt at 210 was not acknowledged. Therefore Device A can adjust the delay after the R-wave detection, shown at 216, by increasing or decreasing the delay. Here, Device A adjusts such that the next attempt in which data packet 220 is sent occurs with a greater delay 226. This time, the T-wave 224 is missed, and the data packet 220 is received and acknowledged by Device B at 222. As illustrated by FIGS. 4-6, not only are there multiple characteristics to be potentially aware of, but also multiple conditions within the characteristics.

For purposes herein, the ECG, transthoracic impedance, and status of the respiration cycle are three possible characteristics. Another characteristic may include posture, which may be determined by use of an accelerometer or through analysis of some other signal such as skeletal muscle activity, the shape or amplitude of a respiration signal, or ECG morphology from one or more sensing vectors. If the patient is exercising, there may be a detectable cycle associated with motion artifacts generated with the patient's stride. For example, at each foot-strike if the patient is running, a monitored biological electrical signal or a monitored accelerometer output, for example, may demonstrate a motion artifact. Testing communication success relative to the detected motion artifact may be useful in determining whether and how communication success can be ensured when the artifact is identified. In some examples, the QRS and cardiac signal may actually not be of significant importance to communication success, and other factors may be deemed more likely to create marginal or poor communication, such as those non-ECG items just noted.

It should be noted in this context that an implantable medical device communication system may have multiple reasons for communicating. Some communication is not urgent, as for example, a periodic device status check communication. Other communication is urgent, as for example, a request that a device deliver therapy or prepare to have therapy delivered by a second device. A specific example would be the combination of an LCP and SICD, where the SICD may non-urgently request battery status from the LCP periodically (i.e. weekly), and may on occasion urgently request that the LCP provide a beat rate measurement confirmation prior to the SICD delivering a high power defibrillation shock to the patient, where the LCP rate measurement confirmation would be used to prevent inappropriate shocks due to malsensing.

For another example, an SICD used in combination with a spinal cord stimulator (SCS) may use an urgent communication to allow the SICD to warn the SCS that a high energy defibrillation shock, which could overwhelm the SCS sensing circuitry inputs, is about to be delivered so that the SCS can suspend sensing or isolate its sensing circuitry during the shock. Temporal optimization may be performed using the non-urgent communication requests, to give greater confidence that an urgent request will be received successfully.

FIGS. 7-11 are flow diagrams of a several illustrative methods that may be implemented by a medical device or medical device system. Starting with FIG. 7, the illustrative method begins with identifying a characteristic at 250, then selecting a condition at 252 to assess for its potential impact on communication. Next, the condition and characteristic are monitored and an attempt at communication is made, as shown at 254. The communication effort is then assessed at 256. The assessment at 256 may be a simple pass/fail assessment, or may include a more complex analysis such as review of the signal-to-noise ratio, signal strength, frame or bit error rate, presence or lack of acknowledgement/handshake, presence or lack of an intended response (therapy or other), measurement of link availability or speed, or other feature of the communication attempt, for example as discussed in commonly assigned U.S. Provisional Patent Application 62/134,726, filed Mar. 18, 2015 and titled COMMUNICATIONS IN A MEDICAL DEVICE SYSTEM WITH LINK QUALITY ASSESSMENT the disclosure of which is incorporated herein by reference.

While several examples rely on electrical signals (myopotential or neuropotential, for example) and potential interference with conducted communication, other combinations are possible. For example, an acoustic communication system may consider heart sounds or respiratory sounds, rather than myopotentials.

Using the assessment at 256, an association can be generated at 258. Steps 252, 254 and 256 may be repeated for other conditions, as indicated at 260, of the same characteristic. In an additional loop indicated at 262, other characteristics may also be assessed. If desired, further combinations of characteristics and conditions may be concatenated for testing as well. Optionally, a probability map may be generated, as indicated at 264. Such a map may include possible communication pathways (such as links and configurations of devices) and sets of probabilities of success given particular parameters, for example. A probability map may be used by an individual device or system to plot out communication strategies, or it may be exported for diagnostic and system design purposes. In addition, as indicated at 266, settings for the system under test may also be generated, including, for example, if-then type rules for planning communication timing relative to identified conditions and characteristics.

For example, the ECG may be identified as a characteristic at 250, and a condition in which the ECG is above a threshold amplitude may be identified, with testing performed at 254 by attempting to communicate a data packet with the ECG at certain amplitude levels, using a looping approach indicated by block 260. Attempts may be made, for example, with the ECG showing an R-wave as one condition, a T-wave as another condition, and being near baseline during the interval between a T-wave and a subsequent P-wave as yet another condition. The attempts are assessed at 256, and an association is constructed at 258. A probability map can be generated at 264. The system can be appropriately set at 266 to provide temporal optimization such that communication attempts occur at times within the ECG cycle selected to maximize the chance of success. As part of the setting step at 266, or the mapping at 264, data may be communicated to other implanted devices regarding the settings to be applied.

If desired and available, variations on the communication signal may also be applied, for example, if variable output signal amplitude or data rate are available, different communication variations may also be applied to assess their effect on communication success. For example, a system may determine whether reducing the data rate or increasing signal amplitude can affect the likelihood of communication success. The same characteristic and condition can be repeatedly tested with different configurations of the communication signal.

Figure 7:
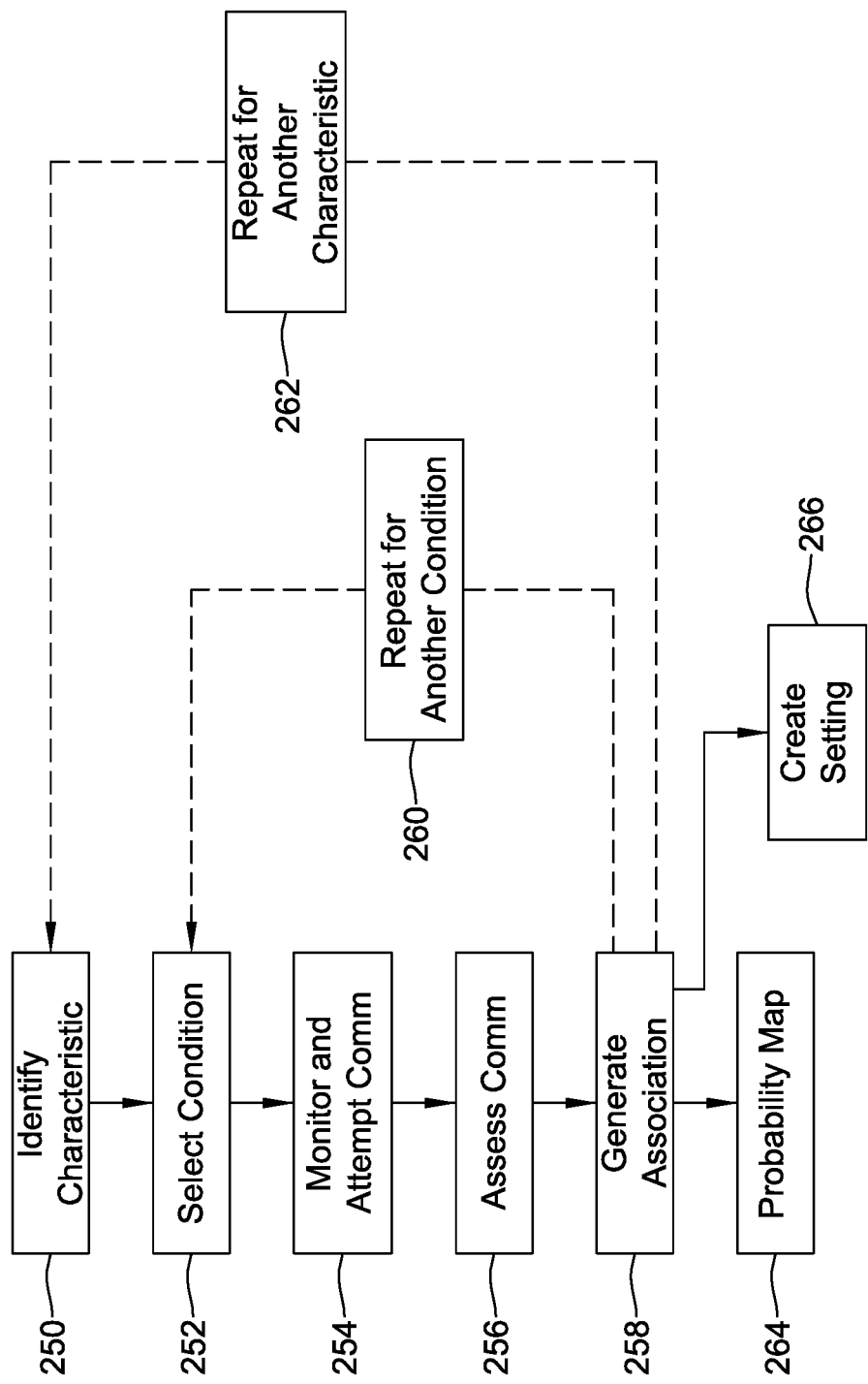

The illustration of FIG. 7 takes a prospective, forward looking approach in which communication ability is assessed under selected conditions. FIG. 8 shows an alternative approach in which, given a particular communication attempt, a backward looking review can be undertaken to troubleshoot failures. In FIG. 8, communication is attempted by sending a data packet from one device to another, as shown at 270. The success, or failure, of the attempt is observed at 272, and then a physiological characteristic and its condition at the time of the communication attempt is observed as noted at 274. A correlation is determined, as shown at 276, and subsequent communication can be planned accordingly by, for example, increasing or reducing a delay relative to an observable phenomenon. The correlation stored at 276 can be tested and retested over time to determine whether it accurately reflects real world conditions.

As an example, with a patient who exercises, there may be a cyclic motion artifact in a detected biological signal associated with the patient's stride, or swim stroke, or other repetitive motion. An attempt at communication is made at 270 and fails at 272. It is then determined at 274 how the failed communication attempt related, in time, to the motion artifact. The motion artifact may be determined by sensing the communication channel or by observing a separately sensed channel. A correlation is presumed at 276 and stored for later reference, and plans are made at 278 to ensure that a subsequent attempt at communication will occur with a different temporal relationship to the motion artifact (if such an artifact is observed). The plan at 278 may then be communicated throughout the system, if desired.

FIG. 9 provides another example. A communication metric, such as amplitude or signal-to-noise ratio, is measured for a given data packet or communication attempt at 300. A potentially related physiological condition is also observed, as shown at 302. A probability of success given the communication metric is generated at 304. The communication strategy is then configured at 306, using the condition of the physiological characteristic observed at 302.

As an example, the respiratory cycle of a patient may be observed by tracking transthoracic impedance over time. A communication attempt may be made and characteristics observed in relation to the communication attempt would be measured in block 300. The status of the respiration cycle is observed using block 302, and mapping of the probability of communication success based on the point in the respiration cycle at which communication is attempted can be generated at 304. Then communication attempts for future use can be configured in block 306.

If, for example, the phase of respiration at which the transthoracic impedance is at a minimum shows better communication metrics than the point of maximum transthoracic impedance, then the map of probability at 304 would be used to configure communications to occur while minimum transthoracic impedance is occurring. On the other hand, the probability mapping at 304 may determine from the observed communication metrics that the respiration cycle is not likely to impact communication success or failure. If that is the case, then a different characteristic and condition may instead be assessed, and the system would record data indicating that a configuration based on respiration cycle may not be helpful.

Figure 10:
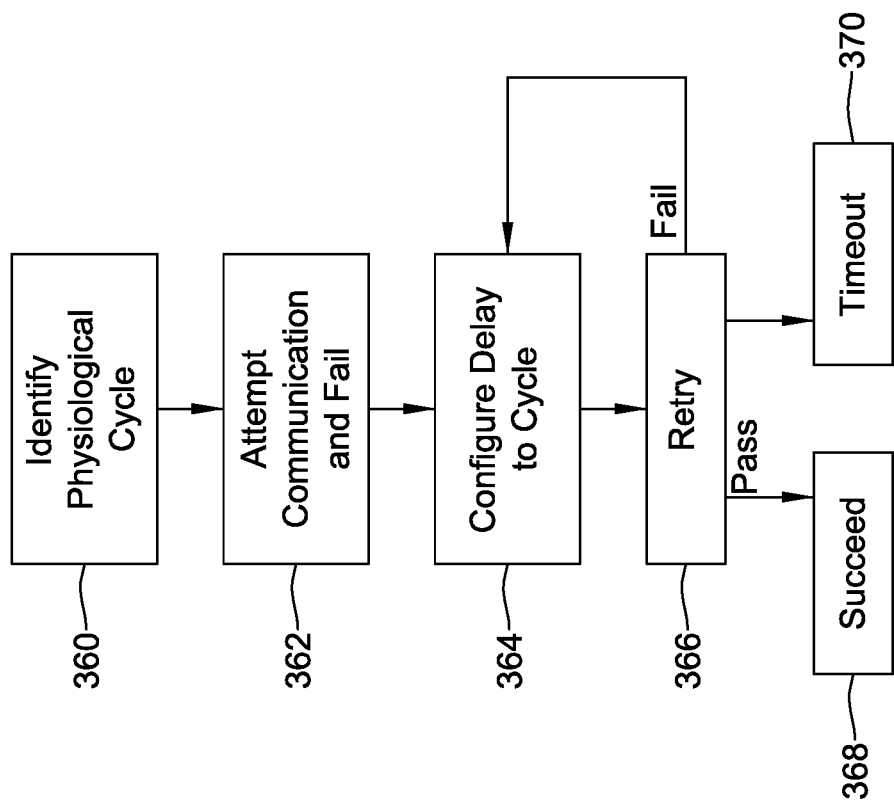

FIG. 10 shows another example. A physiological cycle is identified at 360. Communication is attempted and fails at 362. (Steps 360 and 362 may be reversed with the physiological cycle identified in response to or after failure). A delay relative to an event within the observed cycle is then configured at 364, and a retry scheduled at 366. If the retry fails, the method returns to 364 and configures a different delay relative to the cycle. Multiple retries may be attempted. A retry limit may be enforced, for example, with no more than 3-10 retries (or more or fewer, as desired). Eventually the system either retries to success at 368, or reaches a timeout 370 in which case an alert may be set relative to communication difficulty.

Figure 11:
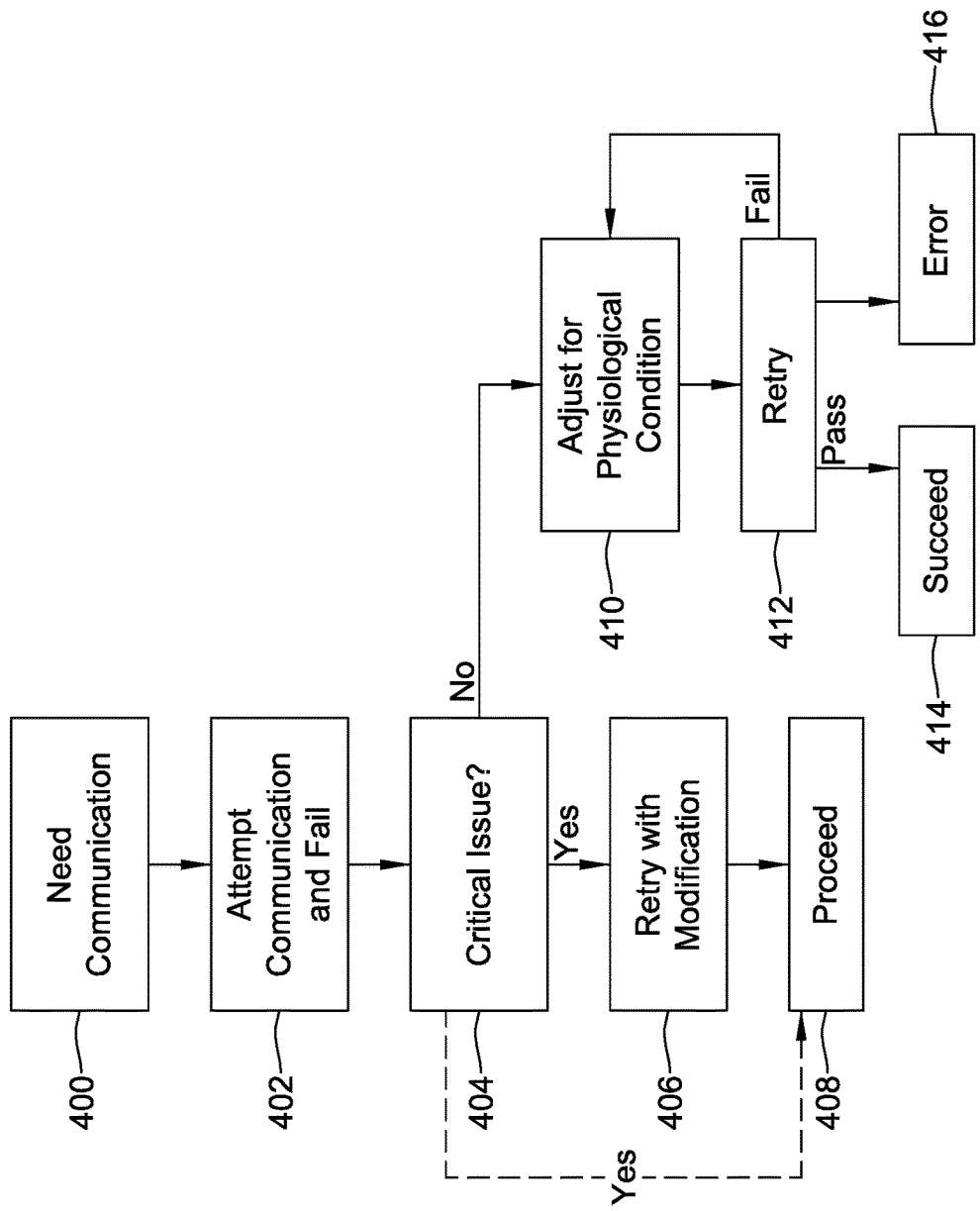

FIG. 11 shows another example in which different treatment is given to critical and non-critical issues. Here, beginning with a need for communication at 400, an attempt is made at 402 and fails. It is then determined whether a critical or urgent issue has arisen at 404. For some urgent issues, the method may execute one or more retries at 406 and then proceed regardless of success, or the retry may be bypassed entirely as indicated by the dashed line.

For example, if an SICD is attempting to cause an LCP to deliver antitachycardia pacing (ATP) because the SICD is about to prepare for defibrillation therapy, no retries may be called if the retry interrupts therapy preparation, as the patient may be suffering a life-threatening situation. On the other hand, if the SICD can attempt to call for ATP without interrupting therapy preparations (which may take several seconds as capacitors are charged to therapy levels), one or several retries 406 may be attempted during therapy preparation.

If a non-critical issue is occurring at 404, then an adjustment is made for a physiological condition at 410 and a number of retries may be attempted in a loop between 410 and 412. Upon success, the parameters 414 of a successful communication attempt would be stored for later use. If the number of retries is limited at 412 and the maximum retry limit is reached, then the system may set an error flag or annunciate an error condition 416.

A first non-limiting example takes the form of a first medical device comprising: means for communicating with a second implantable medical device; means for identifying a first characteristic having a possible impact on communication success; means for selecting a first condition of the first characteristic on which to trigger an attempt at communication; means for determining that the first condition of the first characteristic is present and attempting communication with the second implantable medical device; means for assessing whether the attempted communication was successful; and means for associating the first condition and first characteristic with a reduced likelihood of communication success if the attempted communication was not successful.

In this first non-limiting example, the means for communicating may take the form of, for example, the communication subsystem 62 in FIG. 2, optionally including the antenna 74 or, alternatively, for a conducted communication system, the I/O subsystem 58 of FIG. 2 and one or more of electrodes 64, 66 or 72. The means for identifying a first characteristic condition may include an instruction set or sets for performing a step or steps as described in association with block 250 of FIG. 7, which may be stored in memory 54 of FIG. 2 or which can be performed by a processing circuitry 52, or such means may include dedicated circuitry, for example, of the processing circuitry 52.

Further in the first non-limiting example, the means for selecting a first condition of the first characteristic on which to trigger an attempt at communication may include an instruction set stored in memory 54 for operation by processing circuitry 52 of FIG. 2, instructions embedded in processing circuitry 52 of FIG. 2, or dedicated circuitry of the processing circuitry 52 of FIG. 2, which are configured to perform a step as described in association with block 252 of FIG. 7. Also in the first non-limiting example, the means for determining that the first condition of the first characteristic is present and attempting communication with the second implantable medical device may include an instruction set stored in memory 54 for operation by processing circuitry 52 of FIG. 2, instructions embedded in processing circuitry 52 of FIG. 2, or dedicated circuitry of the processing circuitry 52 of FIG. 2, which are configured to perform a step as described in association with block 255 of FIG. 7, in which the processing circuitry is further configured to direct and/or make use of the communications circuitry 62 and antenna 74 and/or the I/O circuitry 58 and one or more of electrodes 64, 66 or 72.

In the first non-limiting example, the noted means for assessing whether the attempted communication was successful may include an instruction set stored in memory 54 for operation by processing circuitry 52 of FIG. 2, instructions embedded in processing circuitry 52 of FIG. 2, or dedicated circuitry of the processing circuitry 52 of FIG. 2, which are configured to perform a step as described in association with block 256 of FIG. 7. Finally in the first non-limiting example, the means for associating the first condition and first characteristic with a reduced likelihood of communication success if the attempted communication was not successful may include an instruction set stored in memory 54 for operation by processing circuitry 52 of FIG. 2, instructions embedded in processing circuitry 52 of FIG. 2, or dedicated circuitry of the processing circuitry 52 of FIG. 2, which are configured to perform a step as described in association with block 258 of FIG. 7, which is configured for operation in the event the attempted communication is not successful.

An extension of this first non-limiting example may further comprise a means for associating the first condition and first characteristic with an improved likelihood of communication success if the attempted communication was successful, which may include an instruction set stored in memory 54 for operation by processing circuitry 52 of FIG. 2, instructions embedded in processing circuitry 52 of FIG. 2, or dedicated circuitry of the processing circuitry 52 of FIG. 2, which are configured to perform a step as described in association with block 258 of FIG. 7, which is configured for operation in the event the attempted communication is not successful.

Another extension of this first non-limiting example further comprises optimization means for selecting multiple conditions of the first characteristic and repeatedly operating the means for determining, means for assessing and means for associating for each of multiple conditions of the first characteristic to determine whether the first characteristic can be used to determine a likelihood of communication success, wherein the optimization means may include an instruction set stored in memory 54 for operation by processing circuitry 52 of FIG. 2, instructions embedded in processing circuitry 52 of FIG. 2, or dedicated circuitry of the processing circuitry 52 of FIG. 2, which are configured to perform a step as described in association with block 260 of FIG. 7.

Still another extension of this first non-limiting example further comprises a means for identifying a second characteristic, wherein the means for determining, means for assessing and means for assessing are operable to test at least a first condition of the second characteristic to determine whether the second characteristic can be used to determine a likelihood of communication success, wherein the means for identifying a second characteristic may include an instruction set stored in memory 54 for operation by processing circuitry 52 of FIG. 2, instructions embedded in processing circuitry 52 of FIG. 2, or dedicated circuitry of the processing circuitry 52 of FIG. 2, which are configured to perform a step as described in association with block 262 of FIG. 7.

A second non-limiting example takes the form of a first medical device comprising means for communicating with a second medical device; means for determining a first condition of a first characteristic is present; and means for modifying communication with the second implantable medical device based on the determination; wherein at least one of the first and second medical devices is implantable.

In this second non-limiting example, the means for communicating may take the form of, for example, the communication subsystem 62 in FIG. 2, optionally including the antenna 74 or, alternatively, for a conducted communication system, the I/O subsystem 58 of FIG. 2 and one or more of electrodes 64, 66 or 72.

Also in this second non-limiting example, the means for determining a first condition of a first characteristic is present may include an instruction set stored in memory 54 for operation by processing circuitry 52 of FIG. 2, instructions embedded in processing circuitry 52 of FIG. 2, or dedicated circuitry of the processing circuitry 52 of FIG. 2, which are configured to obtain information regarding one or more of the state of the patient's ECG, the patient's measurable impedance, a biological cycle, or other measurable element such as the output of an accelerometer to determine a condition of a first characteristic.

Finally in the second non-limiting example, the means for modifying may include an instruction set stored in memory 54 for operation by processing circuitry 52 of FIG. 2, instructions embedded in processing circuitry 52 of FIG. 2, or dedicated circuitry of the processing circuitry 52 of FIG. 2, which are configured to adjust one or more parameters of a communication subsystem 62 in FIG. 2, optionally including the antenna 74 or, alternatively, for a conducted communication system, the I/O subsystem of FIG. 2.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A first medical device comprising a communication module for communicating with a second implantable medical device and a controller operatively coupled to the communication module for at least one of receiving or transmitting messages, the controller configured to optimize communication by:
    identifying a first characteristic having a possible impact on communication success;
    selecting a first condition of the first characteristic on which to trigger an attempt at communication;
    determining that the first condition of the first characteristic is present and attempting communication with the second implantable medical device;
    assessing whether the attempted communication was successful; and
    if the attempted communication was not successful, associating the first condition and first characteristic with a reduced likelihood of communication success;
    wherein the first characteristic is a status of a cyclic biological phenomenon and the first condition is the occurrence of a recurring event in the cyclic biological phenomenon.

2. The first medical device of claim 1 wherein the communication module is configured for communication by conducted communication.

3. The first medical device of claim 1 wherein the first medical device is configured as an implantable medical device.

4. The first medical device of claim 1, wherein the controller is further configured to associate the first condition and first characteristic with an improved likelihood of communication success if the attempted communication was successful.

5. The first medical device of claim 1, wherein the controller is configured to further optimize communication by selecting multiple conditions of the first characteristic and repeating the determining and assessing steps for each of multiple conditions of the first characteristic to determine whether the first characteristic can be used to determine a likelihood of communication success.

6. The first medical device of claim 1, wherein the controller is configured to identify a second characteristic and test at least a first condition of the second characteristic to determine whether the second characteristic can be used to determine a likelihood of communication success.

7. The first medical device of claim 1, wherein the cyclic biological phenomenon is a cardiac cycle, and the first condition is the occurrence of one of a cardiac R-wave or a cardiac T-wave.

8. The first medical device of claim 1, wherein the cyclic biological phenomenon is a cardiac cycle, and the first condition is the occurrence of a pacing pulse.

9. The first medical device of claim 1, wherein the cyclic biological phenomenon is a respiration cycle, and the first condition is the occurrence of one of an exhale or an inhale.

10. The first medical device of claim 1, wherein the cyclic biological phenomenon is a transthoracic impedance, and the first condition is the occurrence of one of a maximum impedance or a minimum impedance.

11. An implantable medical device system comprising a first medical device as recited in claim 1 and a second implantable medical device configured for communication with the first medical device, wherein the first medical device is an intracardiac pacing device, and the second implantable medical device is a subcutaneous defibrillator.

12. An implantable medical device system comprising a first medical device as recited in claim 1, and a second implantable medical device configured for communication with the first medical device, wherein the first medical device is a subcutaneous defibrillator, and the second implantable medical device is an intracardiac pacing device.

13. A method of communication with an implantable medical device comprising:
    identifying a characteristic having a possible impact on communication success;
    selecting a condition of the characteristic on which to trigger an attempt at communication;
    attempting communication based on the condition of the characteristic occurring;
    assessing whether the communication was likely successful and:
        if the communication was successful, associating the characteristic and condition with an improved likelihood of communication success; or
        if the communication was not successful, associating the characteristic and condition with a reduced likelihood of communication success; and
    configuring the implantable medical device to monitor the characteristic for occurrence of the condition and avoid communication in response thereto if the characteristic and condition are associated with a reduced likelihood of communication success;
    wherein the characteristic is a cyclic biological phenomenon and the condition is the occurrence of a recurring event in the cyclic biological phenomenon.

14. The method of claim 13 further comprising configuring the implantable medical device to monitor the characteristic for occurrence of the condition and communicate in response thereto if the characteristic and condition are associated with an improved likelihood of communication success.

15. The method of claim 13, wherein the cyclic biological phenomenon is one of a respiration cycle or a cardiac cycle.

16. The method of claim 13 wherein the cyclic biological phenomenon is a cardiac cycle and the first condition is the occurrence of one of a cardiac R-wave or a cardiac T-wave.

17. The method of claim 13 wherein the cyclic biological phenomenon is a cardiac cycle and the first condition is the occurrence of a pacing pulse.

18. The method of claim 13 wherein the cyclic biological phenomenon is a respiration cycle and the first condition is the occurrence of one of an exhale or an inhale.

19. The method of claim 13 wherein the cyclic biological phenomenon is a transthoracic impedance, and the first condition is the occurrence of one of a maximum impedance or a minimum impedance.

* * * * *